(12) United States Patent
Imamura

(10) Patent No.: US 11,147,446 B2
(45) Date of Patent: Oct. 19, 2021

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventor: Hiroshi Imamura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 498 days.

(21) Appl. No.: 16/120,052

(22) Filed: Aug. 31, 2018

(65) Prior Publication Data

US 2019/0069772 A1 Mar. 7, 2019

(30) Foreign Application Priority Data

Sep. 7, 2017 (JP) .............................. JP2017-172339

(51) Int. Cl.
*A61B 3/00* (2006.01)
*A61B 3/10* (2006.01)

(52) U.S. Cl.
CPC .......... *A61B 3/0025* (2013.01); *A61B 3/0041* (2013.01); *A61B 3/102* (2013.01)

(58) Field of Classification Search
CPC ..... A61B 3/0025; A61B 3/102; A61B 3/0041; A61B 3/1225; A61B 3/14
USPC ....................................................... 351/206
See application file for complete search history.

(56) References Cited

U.S. PATENT DOCUMENTS

| 2015/0342456 A1 | 12/2015 | Yamashita |
| 2015/0374227 A1 | 12/2015 | Takeno |
| 2016/0066779 A1* | 3/2016 | Imamura .............. A61B 3/0041 351/206 |
| 2016/0150954 A1 | 6/2016 | Furuuchi |

FOREIGN PATENT DOCUMENTS

| CN | 102599882 A | 7/2012 |
| CN | 103251383 A | 8/2013 |
| JP | 2005006894 A | 1/2005 |
| JP | 2014090748 A | 5/2014 |
| JP | 2014140488 A | 8/2014 |
| JP | 2016010657 A | 1/2016 |
| JP | 2017-006179 A | 1/2017 |

* cited by examiner

*Primary Examiner* — James C. Jones
(74) *Attorney, Agent, or Firm* — Canon U.S.A., Inc. IP Division

(57) ABSTRACT

An information processing apparatus including an acquisition unit configured to acquire a first three-dimensional optical coherence tomography (OCT) image of a target eye, and a display control unit configured to display, on a display unit, the first three-dimensional OCT image and an interface configured to receive an instruction for acquiring a second three-dimensional OCT image of the target eye, which is an image captured with a fixation target position the same as a fixation target position used in capturing the first three-dimensional OCT image and is to be combined with the first three-dimensional OCT image.

12 Claims, 21 Drawing Sheets

FIG.5A

Examination Set Settings — 500

| Examination Set List: | Examination Set Name: — 501 |
|---|---|
| AMD | AMD |
| Diabetic Retinopathy | Scan Mode: |
| Glaucoma | OCTA ▶ — 502 |
| | |
| | Scan Pattern: ▶ Small Square |
| | Scan Size: ▶ 3 × 3 mm |
| | Distance between B-scans: ▶ 0.01 |
| | Scanning Direction: ▶ Horizontal |
| | Fixation Position: ▶ Macula |
| | C-Gate Orientation: ▶ Vitreous |
| | B-scans per Cluster: ▶ 3 |
| | — 503 |
| | Add — 504 |

505

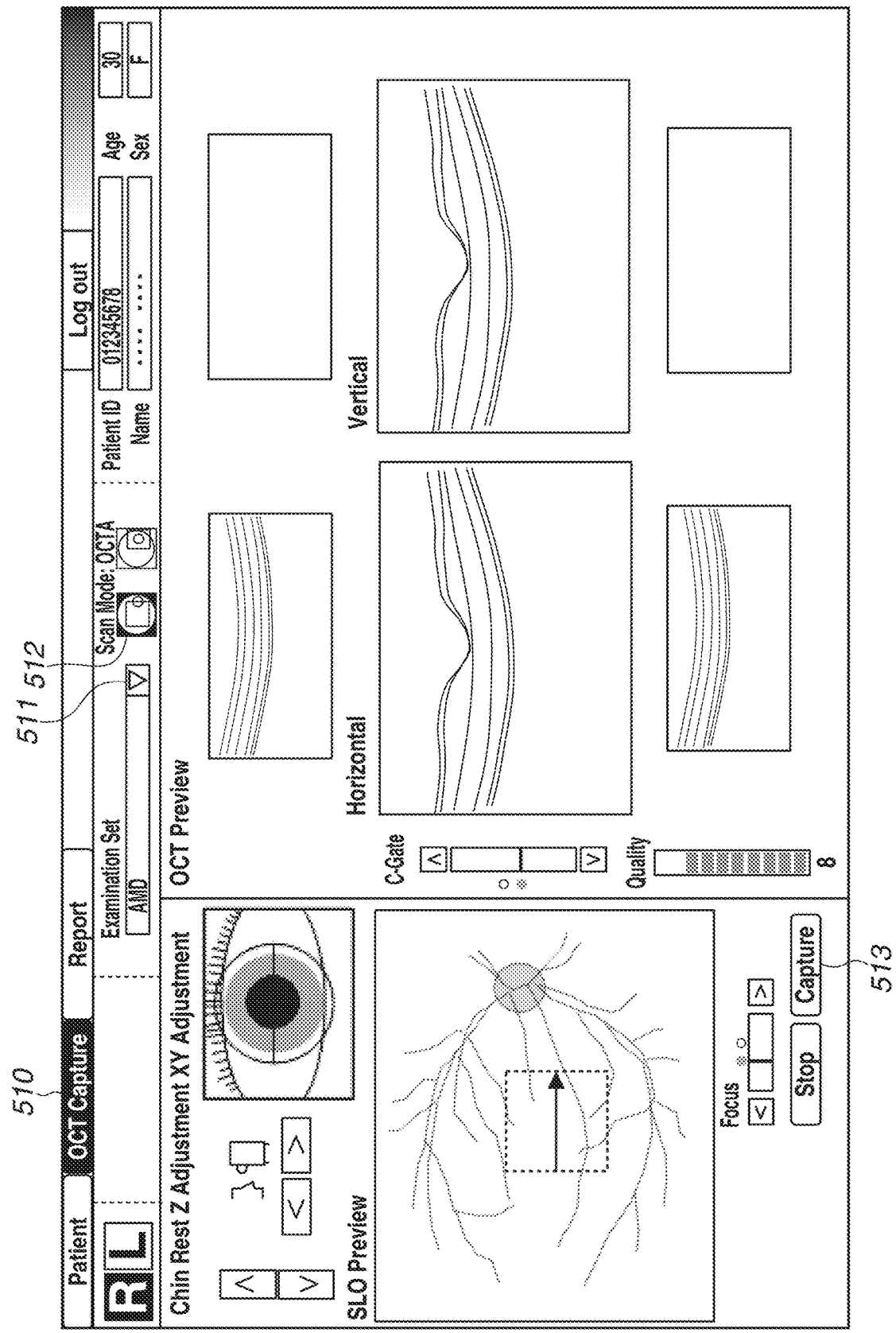

FIG. 8A

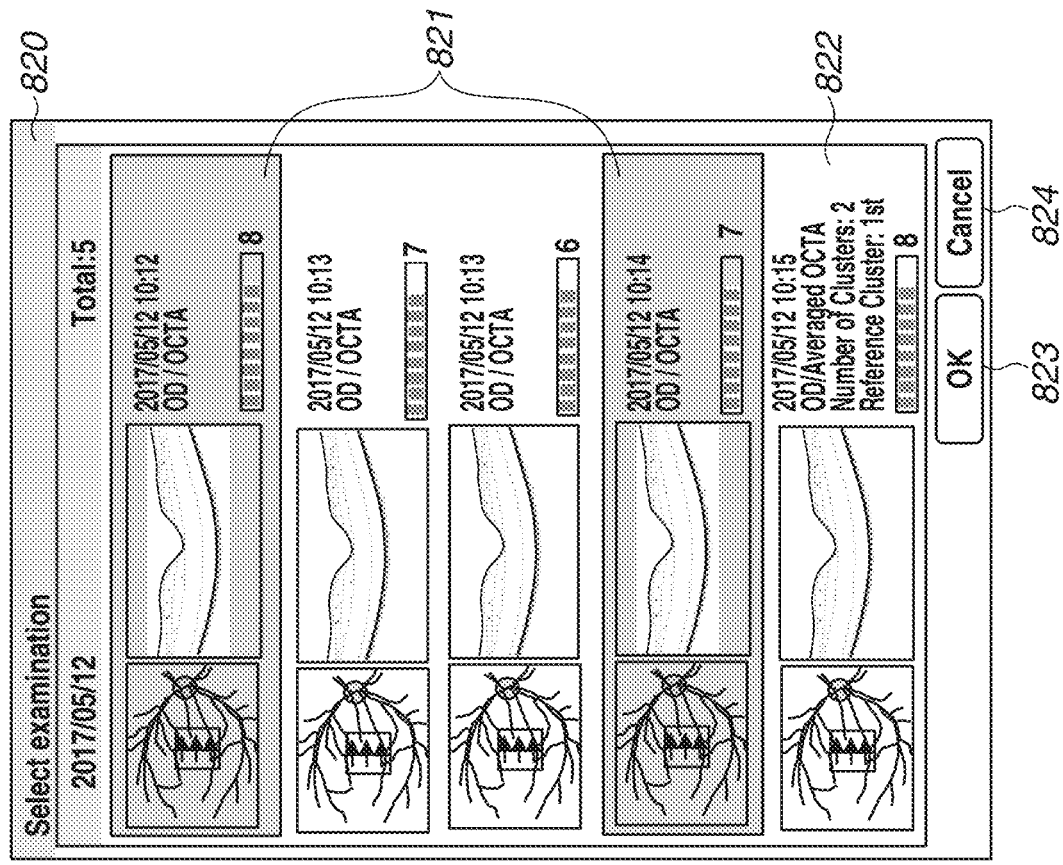
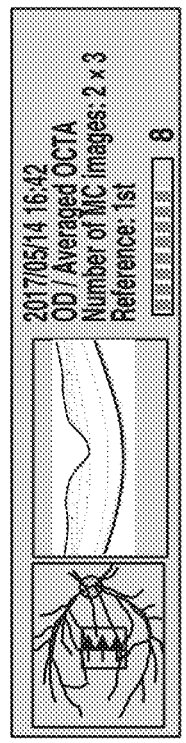
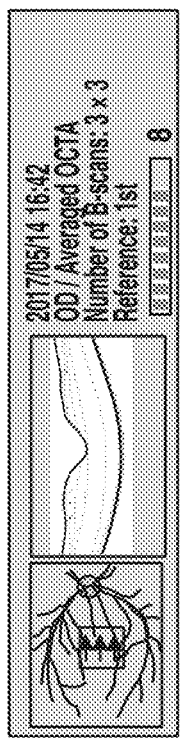
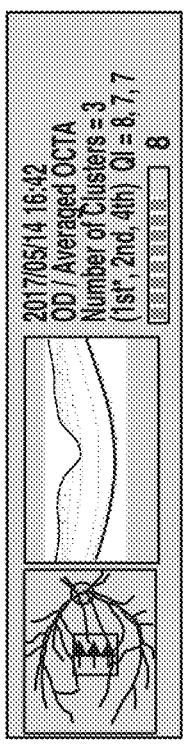
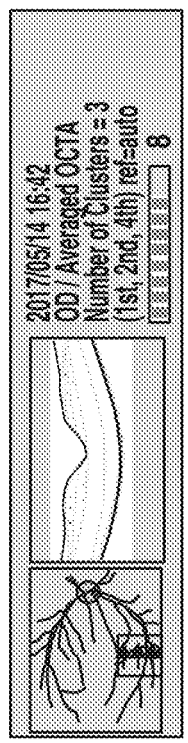

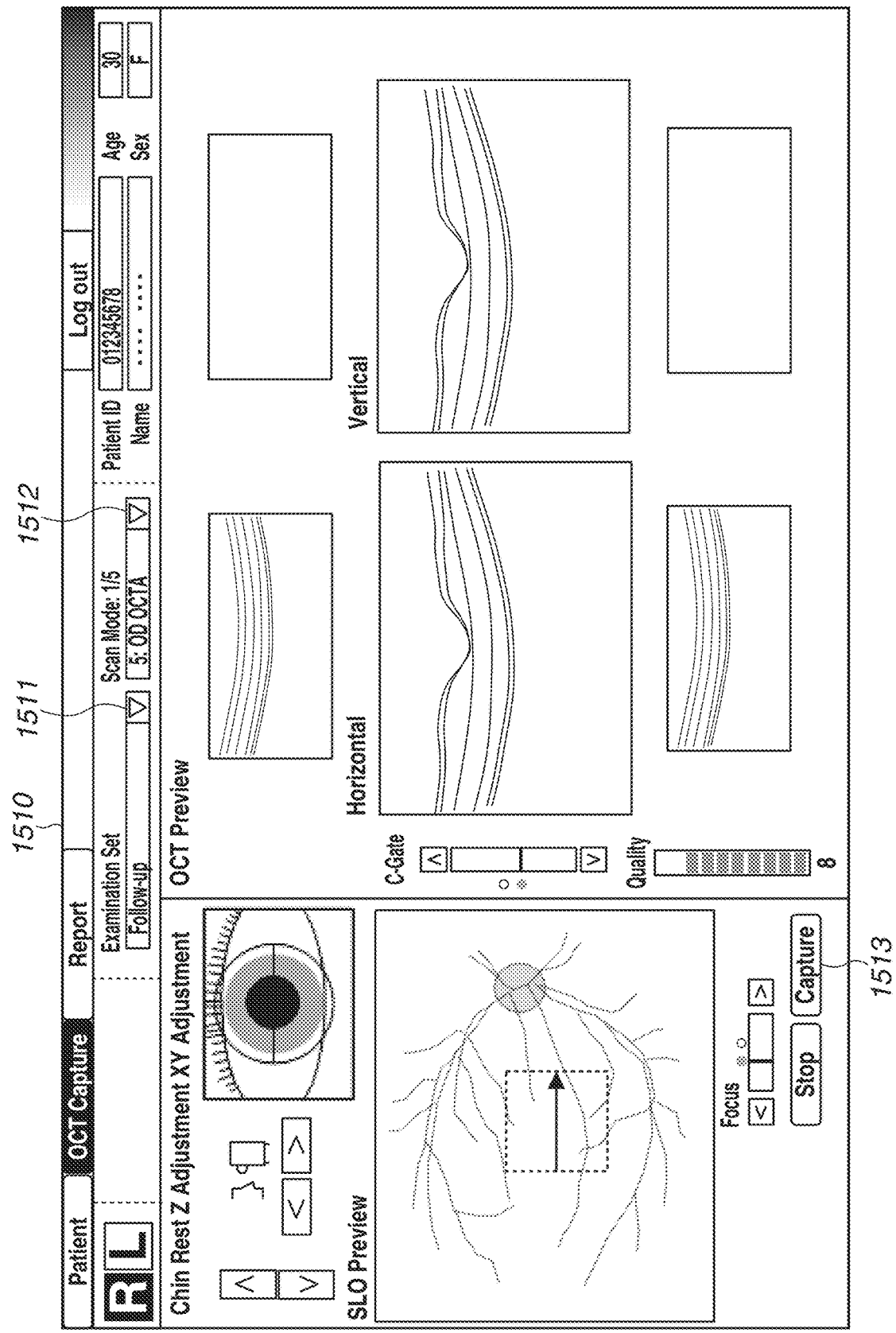

INFORMATION PROCESSING APPARATUS, INFORMATION PROCESSING METHOD, AND STORAGE MEDIUM

BACKGROUND OF THE INVENTION

Field of the Invention

The present disclosure relates to an information processing apparatus, an information processing method, and a storage medium.

Description of the Related Art

In ophthalmologic examinations using optical coherence tomography (OCT), invasive fundus fluorescein angiography examinations are conducted to determine the clinical condition of fundus vessels. In recent years, OCT angiography (OCTA) techniques for non-invasively imaging fundus vessels in three dimensions using OCT have been increasingly used. In OCTA, a plurality of scans with measurement light is performed at the same position and the motion contrast obtained by the interaction between the displacement of red blood cells and the measurement light is imaged.

Japanese Patent Application Laid-Open No. 2017-006179 discusses a technique that discards acquired OCT data and conducts imaging again upon pressing a retry button in a case in which it is judged that the motion contrast imaging is performed inadequately.

However, any user interface suitable for imaging for combining images to improve the image quality is not disclosed.

There is a need in the art for a user interface suitable for imaging for combining images captured at the same site, for example, motion contrast images.

SUMMARY OF THE INVENTION

According to an aspect of the present disclosure, an information processing apparatus includes an acquisition unit configured to acquire a first three-dimensional optical coherence tomography (OCT) image of a target eye, and a display control unit configured to display on a display unit the first three-dimensional OCT image and an interface configured to receive an instruction for acquiring a second three-dimensional OCT image of the target eye which is an image captured with a same fixation target position as a fixation target position used in capturing the first three-dimensional OCT image and is to be combined with the first three-dimensional OCT image.

Further features of the present disclosure will become apparent from the following description of exemplary embodiments with reference to the attached drawings.

BRIEF DESCRIPTION OF THE DRAWINGS

FIGS. 5A and 5B are diagrams respectively illustrating examples of an imaging condition setting screen and an imaging screen displayed on a display unit according to the first exemplary embodiment.

FIGS. 8A to 8F are diagrams each illustrating an example of a report screen displayed on the display unit in step S316 according to the first exemplary embodiment.

FIG. 9 is a diagram illustrating an example of the report screen displayed on the display unit in step S316 according to the first exemplary embodiment.

FIGS. 15A and 15B are diagrams respectively illustrating an example of a baseline test selection screen and an imaging screen displayed on the display unit according to the third exemplary embodiment.

DESCRIPTION OF THE EMBODIMENTS

Figure 4:
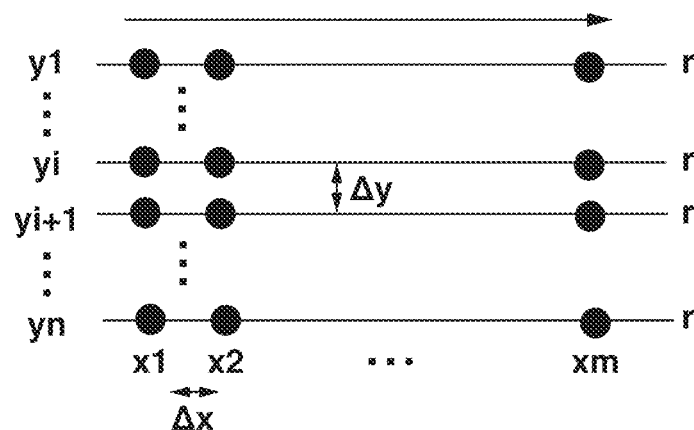
FIG. 4 is a diagram illustrating an example of a scan method of optical coherence tomography angiography (OCTA) imaging according to an exemplary embodiment.

In an information processing apparatus according to a first exemplary embodiment, an operator issues an instruction whether to continue or not continue "repeat optical coherence tomography angiography (OCTA) imaging" by selecting a "repeat imaging button" based on progress information displayed on an imaging check screen. Now, a case where a group of motion contrast images to be used to generate a target high-contrast combined motion contrast image is acquired in response to the instruction will be described. First, an OCTA imaging method will be described below with reference to FIG. 4. FIG. 4 illustrates an example of OCTA imaging in which a main scan direction is a horizontal (x-axis) direction and B-scans are performed r times consecutively at each position (yi; $1 \leq i \leq n$) in a sub-scan direction (y-axis direction). Performing a plurality of scans at the same position in OCTA imaging will be referred to as "cluster scan", and a plurality of tomographic images acquired at the same position will be referred to as "cluster". It is known that generating motion contrast data in cluster units and increasing the number of tomographic images per cluster (the number of scans performed at the same position) improves the contrast of OCTA image (motion contrast image).

An information processing system including an information processing apparatus according to the first exemplary embodiment will be described below with reference to the drawings.

Figure 2A:
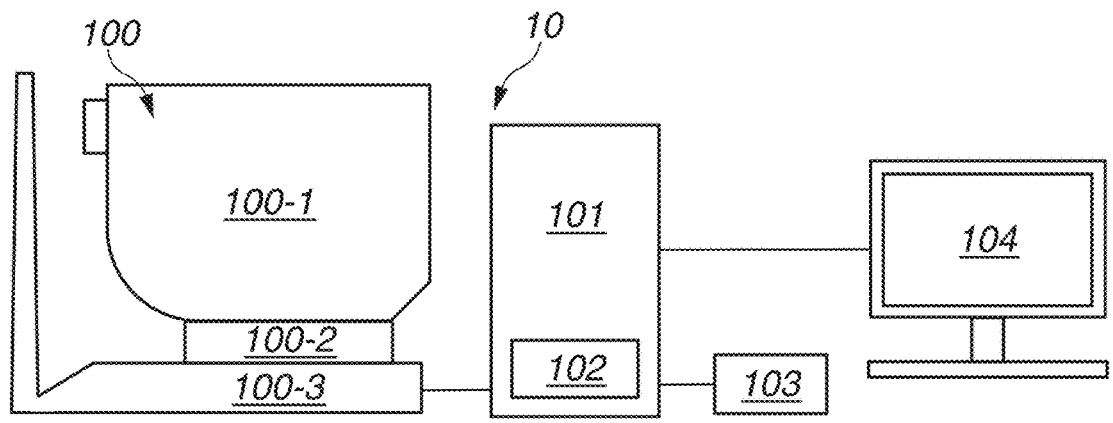
FIGS. 2A and 2B are diagrams illustrating an example of an information processing system and an optical measurement system included in a tomographic imaging apparatus constituting the information processing system, according to an exemplary embodiment.

FIG. 2A illustrates a configuration of an information processing system 10 including an information processing apparatus 101 according to the present exemplary embodiment. As illustrated in FIG. 2A, the information processing system 10 includes the information processing apparatus 101 connected with a tomographic imaging apparatus 100 (also referred to as "OCT"), an external storage unit 102, an input unit 103, and a display unit 104 via an interface.

The tomographic imaging apparatus 100 is an apparatus configured to capture a tomographic image of an eye portion. In the present exemplary embodiment, a spectral domain OCT (SD-OCT) is used as the tomographic imaging apparatus 100. Alternatively, for example, a swept source OCT (SS-OCT) can be used.

In FIG. 2A, an optical measurement system 100-1 is an optical system configured to acquire an image of an anterior eye portion, a scanning laser ophthalmoscopy (SLO) fundus image of a target eye (eye to be examined), and a tomographic image. A stage unit 100-2 enables the optical measurement system 100-1 to move forward, backward, leftward, rightward, upward, and downward. A base unit 100-3 includes a built-in spectrometer described below.

The information processing apparatus 101 is a computer configured to control the stage unit 100-2, control an alignment operation, execute reconstruction of a tomographic image, and the like. The external storage unit 102 stores a program for tomographic imaging, patient information, imaging data, statistical values of normal eye database, and the like.

The input unit 103 is a device with which an operator issues an instruction to the computer. More specifically, the input unit 103 includes a keyboard and a mouse. The display unit 104 is a device configured to display an image, and the like and includes a monitor.

<Configuration of Tomographic Imaging Apparatus>

Figure 2B:
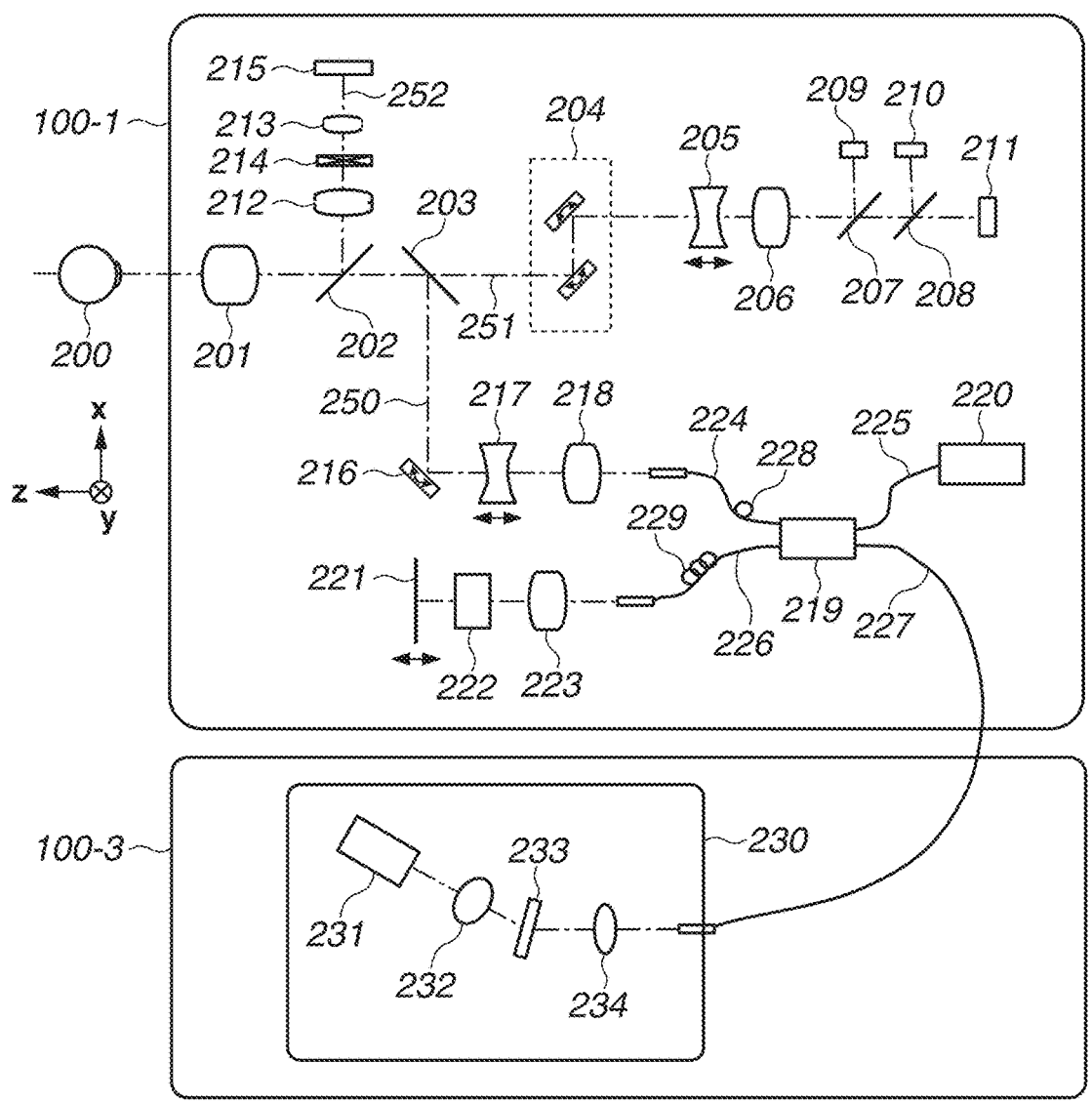

Configurations of an optical measurement system and the spectrometer in the tomographic imaging apparatus 100 according to the present exemplary embodiment will be described below with reference to FIG. 2B.

First, the inside of the optical measurement system 100-1 will be described. An objective lens 201 is arranged to face a target eye 200, and a first dichroic mirror 202 and a second dichroic mirror 203 are arranged on an optical axis of the objective lens 201. The dichroic mirrors 202 and 203 divide the optical path according to wavelength bands into an optical path 250 for an optical coherence tomography (OCT) optical system, an optical path 251 for a SLO optical system and a fixation lamp, and an optical path 252 for observing an anterior eye portion.

The optical path 251 for the SLO optical system and the fixation lamp includes a SLO scan portion 204, lenses 205 and 206, a mirror 207, a third dichroic mirror 208, an avalanche photodiode (APD) 209, a SLO light source 210, and a fixation lamp 211.

The mirror 207 is a prism with a perforated mirror or hollow mirror deposited thereon and separates illumination light from the SLO light source 210 and returned light from the target eye 200. The third dichroic mirror 208 divides the optical path of the SLO light source 210 and the optical path of the fixation lamp 211 according to wavelength bands.

The SLO scan portion 204 scans the target eye 200 with light emitted from the SLO light source 210 and includes an X-scanner and a Y-scanner. The X-scanner performs scanning in an X-direction, and the Y-scanner performs scanning in a Y-direction. In the present exemplary embodiment, the X-scanner includes a polygon mirror because the X-scanner needs to perform scanning at high speed, whereas the Y-scanner includes a Galvano mirror.

The lens 205 is driven by a motor (not illustrated) in an optical axis direction to adjust focus of the SLO optical system and the fixation lamp 211. The SLO light source 210 generates light having a wavelength near 780 nm. The APD 209 detects returned light from the target eye 200 irradiated with light from the SLO light source 210. The fixation lamp 211 generates visible light and presents the visible light to an examinee to prompt the examinee to fixate the target eye 200.

Light emitted from the SLO light source 210 is reflected at the third dichroic mirror 208, travels through the mirror 207, passes through the lens 206 and 205, and is scanned on the target eye 200 by the SLO scan portion 204. Returned light from the target eye 200 travels back through the same path as the illumination light and is then reflected by the mirror 207 and guided to the APD 209, and an SLO fundus image is acquired.

Light emitted from the fixation lamp 211 is transmitted through the third dichroic mirror 208 and the mirror 207 and passes through the lens 206 and 205, and the SLO scan portion 204 forms the light into a predetermined shape at any position on the target eye 200 to prompt fixation of the target eye 200.

On the optical path 252 for observing anterior eye portions are disposed lenses 212 and 213, a split prism 214, and a charge-coupled device (CCD) sensor 215 that detects infrared light for observing anterior eye portions. The CCD sensor 215 has a sensitivity near the wavelength of irradiation light (not illustrated) for observing anterior eye portions, specifically near 970 nm. The split prism 214 is arranged at a position conjugate with the pupil of the target eye 200, and the distance of the optical measurement system 100-1 in a Z-axis direction (optical axis direction) with respect to the target eye 200 is detectable as a split image of the anterior eye portion.

The optical path 250 of the OCT optical system constitutes the OCT optical system as described above and is for imaging tomographic images of the target eye 200. More specifically, the optical path 250 is for acquiring interference signals for forming tomographic images. An XY-scanner 216 is configured to scan the target eye 200 with light. While the XY-scanner 216 is illustrated as a single mirror in FIG. 2B, the XY-scanner 216 includes two Galvano mirrors for respectively performing scans in two axial directions (i.e., X-axis and Y-axis directions).

From between lenses 217 and 218, the lens 217 is driven by a motor (not illustrated) to focus light from an OCT light source 220 emitted from a fiber 224 connected to an optical coupler 219 on the target eye 200. This focusing causes the returned light from the target eye 200 to be formed into a spot on the leading edge of the fiber 224 and to enter the fiber 224.

Next, the optical path from the OCT light source 220, a reference optical system, and a configuration of a spectrometer will be described below. FIG. 2B includes the OCT light source 220, a reference mirror 221, a dispersion compensation glass 222, a lens 223, the optical coupler 219, single-mode optical fibers 224 to 227 connected to the optical coupler 219 and integrated together, and a spectrometer 230.

The above-described components configure a Michelson interferometer. Light emitted from the OCT light source 220 enters the optical coupler 219 through the optical fiber 225 and is divided into measurement light on the optical fiber 224 side and reference light on the optical fiber 226 side. The measurement light is applied to the target eye 200, which is an observation target, through the optical path 250 of the OCT optical system and reflected and scattered by the target eye 200 to travel back through the same optical path to the optical coupler 219.

On the other hand, the reference light travels through the optical fiber 226, the lens 223, and the dispersion compensation glass 222, which is inserted to adjust the wavelength dispersion of the measurement light and the reference light, to reach the reference mirror 221 and is reflected thereat. Then, the light travels back through the same optical path to the optical coupler 219.

The measurement light and the reference light are combined by the optical coupler 219 to generate interference light.

Interference occurs when the optical path length of the measurement light and the optical path length of the reference light become substantially equal. The reference mirror 221 is held adjustably in the optical axis direction by a motor (not illustrated) and a driving mechanism (not illustrated), and the optical path length of the reference light is adjustable to the optical path length of the measurement light. The interference light is guided through the optical fiber 227 to the spectrometer 230.

Further, polarization adjustment portions 228 and 229 are disposed in the optical fibers 224 and 226, respectively, and perform polarization adjustment. The polarization adjustment portions 228 and 229 include several portions formed by the optical fibers 224 and 226 being looped. The looped portions are rotated about the lengthwise directions of the optical fibers 224 and 226 to twist the optical fibers 224 and 226 so that the polarization states of the measurement light and the reference light are respectively adjusted to be the same.

The spectrometer 230 includes lenses 232 and 234, a grating 233, and a line sensor 231. The interference light emitted from the optical fiber 227 is changed into parallel light through the lens 234 and then diffracted at the grating 233 and focused on the line sensor 231 by the lens 232.

Next, the OCT light source 220 will be described. The OCT light source 220 is a super luminescent diode (SLD) light source, which is a typical low-coherent light source. The center wavelength is 855 nm, and the wavelength bandwidth is about 100 nm. The bandwidth is an important parameter because the bandwidth affects the resolution of acquired tomographic images in the optical axis direction.

As to the type of the light source, while the SLD light source is selected in the present exemplary embodiment, any light source capable of emitting low-coherent light can be used, and a light source such as an amplified spontaneous emission (ASE) light source, and the like can be used. Since the eyes are measured, the center wavelength is desirably near-infrared light. Further, the center wavelength is desirably as short wavelength as possible because the center wavelength affects the resolution of acquired tomographic images in the widthwise direction. For these reasons, the center wavelength is determined to be 855 nm.

While the Michelson interferometer is used as an interferometer in the present exemplary embodiment, a Mach-Zehnder interferometer can also be used. In a case in which the difference in light quantity between the measurement light and the reference light is large, it is desirable to use a Mach-Zehnder interferometer. In a case in which the difference in light quantity between the measurement light and the reference light is relatively small, it is desirable to use a Michelson interferometer.

<Configuration of Information Processing Apparatus>

Figure 1:
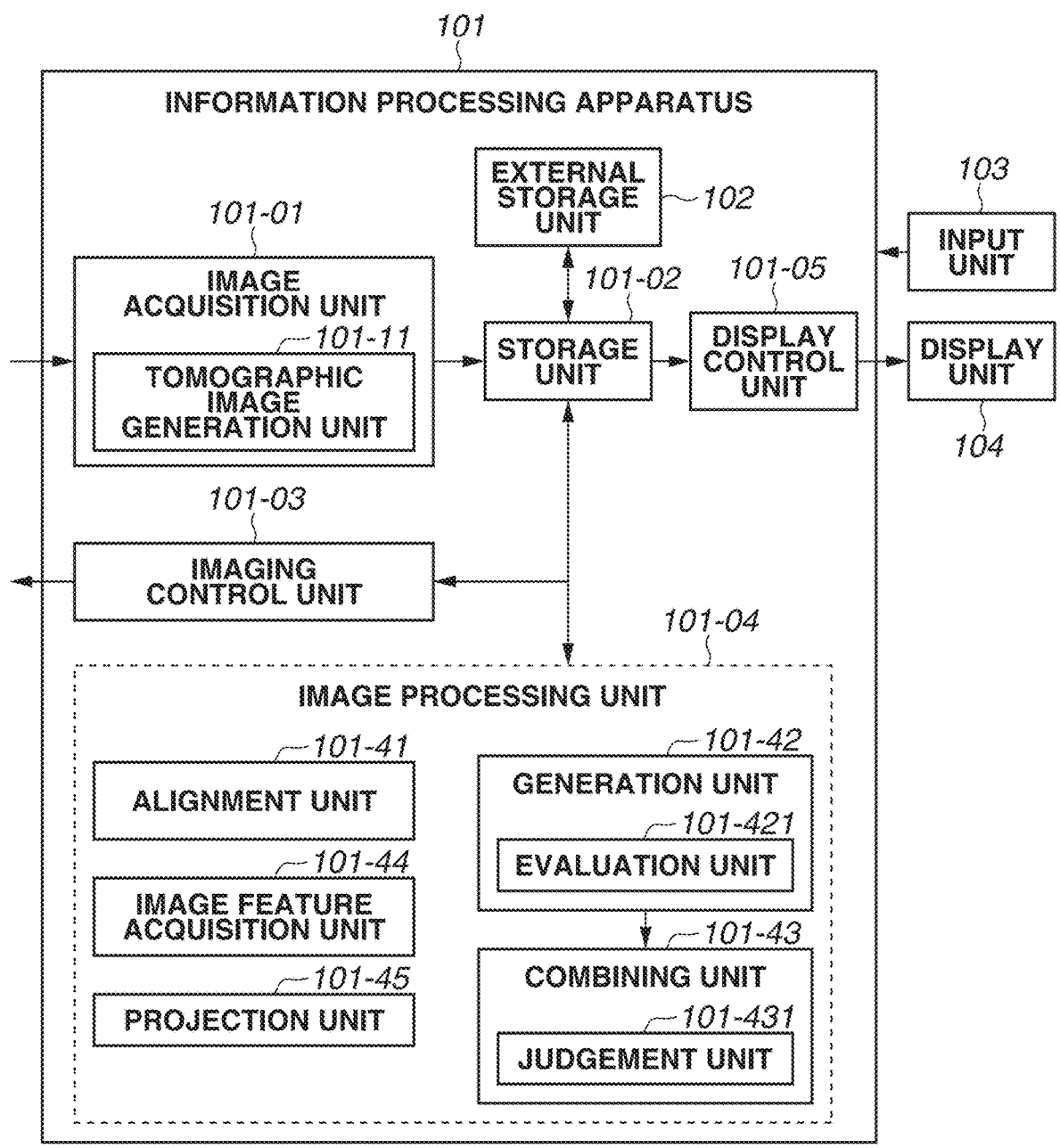
FIG. 1 is a block diagram illustrating an example of a configuration of an information processing apparatus according to a first exemplary embodiment.

A configuration of the information processing apparatus 101 according to the present exemplary embodiment will be described below with reference to FIG. 1.

The information processing apparatus 101 is a personal computer (PC) connected to the tomographic imaging apparatus 100 and includes an image acquisition unit 101-01, a storage unit 101-02, an imaging control unit 101-03, an image processing unit 101-04, and a display control unit 101-05. Further, a central processing unit (CPU) of the information processing apparatus 101 executes software modules for realizing the image acquisition unit 101-01, the imaging control unit 101-03, the image processing unit 101-04, and the display control unit 101-05 to implement the functions thereof. The present exemplary embodiment is not limited thereto and, for example, the image processing unit 101-04 may be realized by dedicated hardware such as an application-specific integrated circuit (ASIC), and the display control unit 101-05 may be realized using a dedicated processor different from the CPU, such as a graphics processing unit (GPU). The CPU and the GPU may be used in combination. Further, a plurality of CPUs or a plurality of GPUs may be used. A program to be executed by the CPU, or other devices is stored in at least one or more memories. Further, the tomographic imaging apparatus 100 and the information processing apparatus 101 may be connected via a network.

The image acquisition unit 101-01 acquires signal data of SLO fundus images and tomographic images captured by the tomographic imaging apparatus 100. Further, the image acquisition unit 101-01 includes a tomographic image generation unit 101-11, generates a tomographic image by acquiring signal data (interference signal) of a tomographic image captured by the tomographic imaging apparatus 100 and then performing signal processing on the acquired signal data, and stores the generated tomographic image in the storage unit 101-02.

The imaging control unit 101-03 performs imaging control on the tomographic imaging apparatus 100. The imaging control includes issuing, to the tomographic imaging apparatus 100, an instruction about imaging parameter settings and an instruction to continue or end repeat imaging.

The image processing unit 101-04 includes an alignment unit 101-41, a generation unit 101-42, a combining unit 101-43, an image feature acquisition unit 101-44, and a projection unit 101-45. For example, the generation unit 101-42 generates three-dimensional motion contrast images. The generation unit 101-42 corresponds to an example of an acquisition unit according to an exemplary embodiment of the present disclosure. The generation unit 101-42 includes an evaluation unit 101-421. The evaluation unit 101-421 may be configured to evaluate the image quality of tomographic images from which motion contrast images are generated, or evaluate the image quality of motion contrast images generated by the generation unit 101-42. The combining unit 101-43 is an example of a combining unit according to an exemplary embodiment of the present disclosure and includes a judgement unit 101-431. The combining unit 101-43 combines a plurality of pieces of motion contrast data generated by the generation unit 101-42 to generate a single motion contrast image illustrating a cross section of the fundus at a predetermined position. The image feature acquisition unit 101-44 analyzes a tomographic image to acquire image features such as layer boundaries. The projection unit 101-45 generates a two-dimensional motion contrast image (en-face image) by performing projection in a predetermined depth range in a three-dimensional motion contrast image. As to a projection method, any method can be used such as a maximum intensity projection (MIP) method or an average intensity projection (AIP) method. Further, the depth range for generating a two-dimensional motion contrast image can be specified based on the acquired layer boundaries. Further, the image feature acquisition unit 101-44 and the projection unit 101-45 may be included in the generation unit 101-42.

The external storage unit 102 holds information (e.g., name, age, sex of the patient) about the target eye 200, captured images (tomographic images, SLO images and OCTA images) and combined images, imaging parameters, combining condition data of the combined images, and operator-set parameters in association with one another. The input unit 103 is, for example, a mouse, a keyboard, and/or a touch operation screen, and the operator issues instructions to the information processing apparatus 101 and the tomographic imaging apparatus 100 via the input unit 103.

Figure 3:
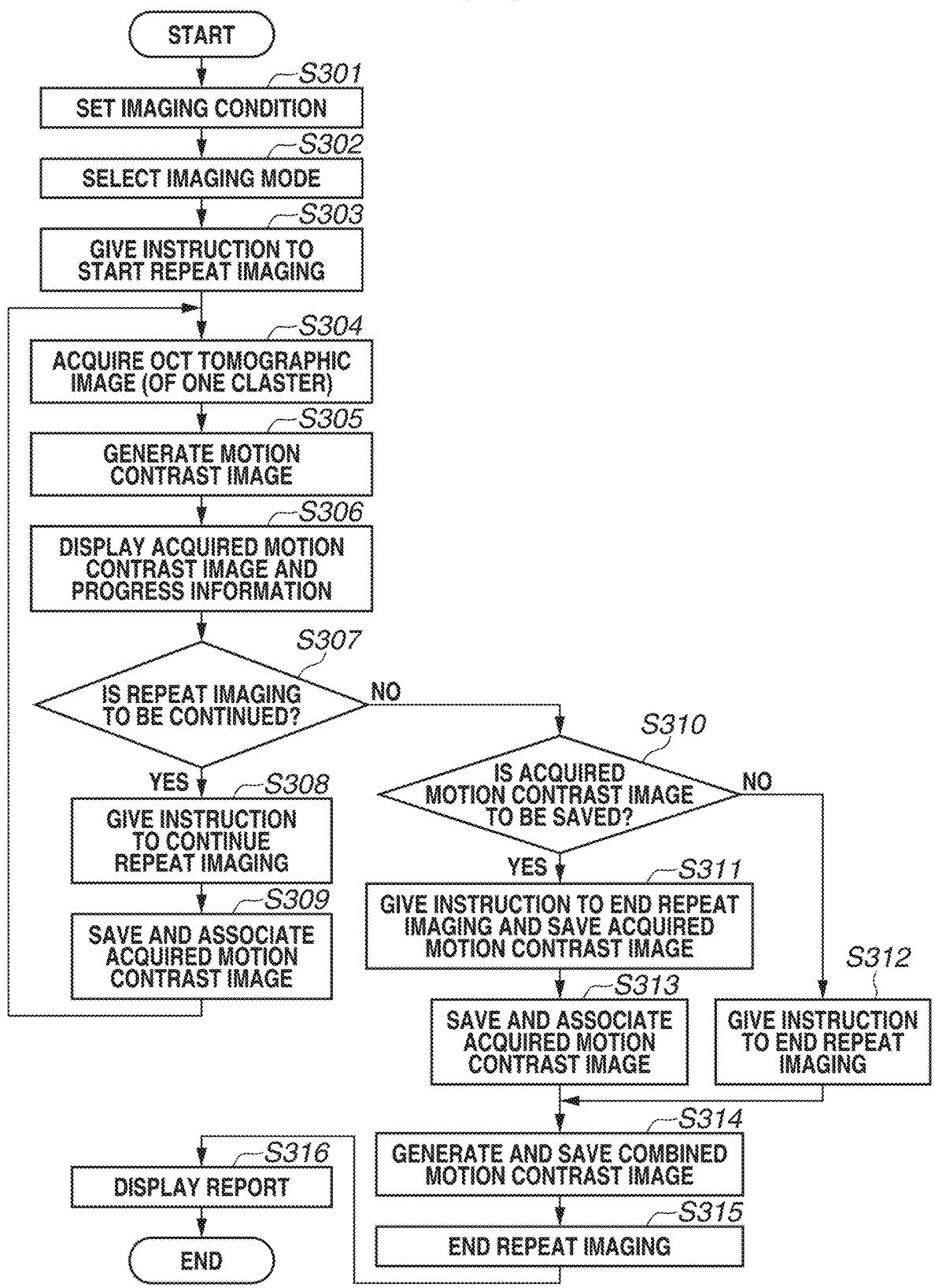
FIG. 3 is a flowchart illustrating an example of processing executed by the information processing system according to the first exemplary embodiment.

Next, a processing procedure of the information processing apparatus 101 according to the present exemplary embodiment will be described below with reference to FIG. 3. FIG. 3 is a flowchart illustrating operation processing of the entire system according to the present exemplary embodiment.

<Step S301>

The operator operates the input unit 103 to set an imaging condition of an OCTA image with respect to the tomographic imaging apparatus 100.

FIG. 5A illustrates an examination set setting screen 500 displayed on the display unit 104. An examination set is also referred to as a protocol or an operation mode and specifies an imaging procedure (including a scan mode) set for each examination purpose. Further, a display method can be set for an OCT image and an OCTA image acquired in each scan mode. The examination set setting screen 500 includes an examination set name input section 501, a scan mode designation section 502, an imaging parameter designation section 503, an add button 504, and an examination set list section 505.

First, the operator operates the input unit 103 to input a name of an examination set to the examination set name input section 501. A predetermined character string can be input as the name of the examination set, and a name that is easy to understand for the operator may be defined. For example, in FIG. 5A, "AMD" is input to define aged macular disease (AMD).

Next, the operator operates the input unit 103 to select a scan mode to be added to the examination set in the scan mode designation section 502. The scan mode designation section 502 is formed as a designation section in the form of a pull-down menu, and the operator can select a scan mode from a plurality of scan modes including an OCTA scan mode. In the present exemplary embodiment, the "OCTA" scan mode that is a scan pattern for OCTA is selected.

Further, the operator operates the input unit 103 to input or select (A) an imaging condition (hereinafter, "imaging condition (A)") about individual OCTA imaging or (B) an imaging condition (hereinafter, "imaging condition (B)") about entire repeat OCTA imaging, through the imaging parameter designation section 503 illustrated in FIG. 5A.

In the present exemplary embodiment, the imaging condition (B) is in the operator's memory. Further, the operator judges whether imaging and a processed image satisfy the imaging condition (B) based on displayed progress information, so that the setting of the imaging condition (B) is not performed and only an instruction with respect to the imaging condition (A) is given on the screen. A method of setting the imaging condition (B) will be described in a second exemplary embodiment.

In the present exemplary embodiment, an instruction is given to specify the following conditions as the imaging condition (A) as illustrated in FIG. 5A.

A-1) scan pattern (Scan Pattern),
A-2) scan region size (Scan Size),
A-3) main scan direction (Scanning Direction),
A-4) scan interval (Distance between B-scans),
A-5) fixation lamp position (Fixation Position),
A-6) coherence gate position (C-Gate Orientation), and
A-7) number of B-scans per cluster (B-scans per Cluster).

The imaging condition (A) is not limited to the above conditions and, for example, an instruction to specify a known imaging parameter can be given, such as the number of A-scans per B-scan.

Lastly, the operator operates the input unit 103 to press the add button 504.

In this way, the examination set including the OCTA scan mode to which the imaging conditions are set with respect to the target eye with the aged macular disease is registered in association with the name "AMD". The registered examination set is stored on the external storage unit 102 and displayed in the examination set list section 505.

<Step S302>

The operator operates the input unit 103 to select a desired examination set through an examination set selection section 511 in an imaging screen 510 illustrated in FIG. 5B and further select a scan mode (included in the desired examination set) through a scan mode selection section 512.

In the present exemplary embodiment, the "AMD" examination set, which is set in step S301 as the examination set, is selected, and the "OCTA" imaging mode is selected as the scan mode.

<Step S303>

The operator operates the input unit 103 to press an imaging start (Capture) button 513 in the imaging screen 510 to give an instruction to start OCTA imaging under the imaging conditions designated in steps S301 and S302.

<Step S304>

The imaging control unit 101-03 issues an instruction to perform OCTA imaging (of one cluster at each scan position) based on the settings designated by the operator to the tomographic imaging apparatus 100 in steps S301 and S302, and the tomographic imaging apparatus 100 acquires a corresponding OCT tomographic image.

In step S304, the tomographic imaging apparatus 100 also performs repeat acquisition of SLO images and executes tracking processing based on an SLO moving image. In the present exemplary embodiment, a reference SLO image used in tracking processing in OCTA imaging is a reference SLO image set in the first OCTA imaging, and a common reference SLO image is used in the case of repeating OCTA imaging. Alternatively, for example, the position of an SLO image may be registered (to the reference SLO image used in the first OCTA imaging) each time OCTA imaging is repeated, and averaging may be performed to update the reference SLO image.

In the present exemplary embodiment, a cluster scan is performed under the imaging condition (illustrated in FIG.

5A) set in step S301. Specifically, three consecutive B-scans are performed at each position in the vertical direction (sub-scan direction) with the horizontal direction being the main scan direction, in a rectangular region of 3×3 mm with the fovea being the imaging center. Further, under the imaging condition illustrated in FIG. 5A, the interval between temporally adjacent cluster scans is 0.01 mm, and OCT tomographic images are acquired with the coherence gate set to the vitreous body side. In the present exemplary embodiment, 300 A-scans constitute one B-scan.

Further, while the repeat OCTA imaging is performed, the same setting values are used (the setting values are not changed) for a right/left eye selection setting and a setting to perform or not perform tracking processing, in addition to the imaging condition set in step S301. For example, while a change of a setting value relating to the imaging such as the fixation target position is received in the first imaging, a change of a setting value relating to the imaging is not received during the imaging after the press of a repeat-imaging-continue button 603. More specifically, the information processing system 10 according to the present exemplary embodiment acquires the second three-dimensional OCT image (image acquired by the second or subsequent imaging) using a setting value identical to a setting value used in acquiring the first three-dimensional OCT image (image acquired by the first imaging) with respect to at least one of a right/left eye selection setting, a main scan direction setting, a scan position setting, a setting of a number of tomographic images to be acquired at a same position, a setting to perform or not perform tracking processing, a setting of a front image for use in tracking, a fixation target position setting, and a coherence gate position setting.

While a change of a setting value relating to the imaging is not received during the imaging after the press of the repeat-imaging-continue button 603 in the above-described example, a warning may be provided if a change of a setting value relating to the imaging is made during the imaging after the press of the repeat-imaging-continue button 603. The warning is realized by, for example, a message or the like displayed on the display unit 104 by the display control unit 101-05. The message to be displayed may be a message that indicates the possibility that the change of the setting value may affect a combined image.

Thus, in the acquisition of the second three-dimensional motion contrast image, the information processing system 10 does not receive an instruction to change the setting, or if an operator instruction to change the setting is received, the information processing system 10 displays a warning on the display unit.

<Step S305>

The image acquisition unit 101-01 and the image processing unit 101-04 generate a motion contrast image based on the OCT tomographic image acquired in step S304.

First, the tomographic image generation unit 101-11 performs wavenumber transform, and fast Fourier transform (FFT), and absolute value transform (acquisition of amplitude) on the interference signals acquired by the image acquisition unit 101-01 to generate a tomographic image of one cluster. Next, the alignment unit 101-41 aligns the tomographic images that belong to the same cluster, and enhance image quality by averaging. The image feature acquisition unit 101-44 acquires layer boundary data from the averaged tomographic images. While a deformable model is used as a method for the layer boundary acquisition in the present exemplary embodiment, any known layer boundary acquisition method may be used. The projection unit 101-45 generates a two-dimensional motion contrast image by, for example, performing projection in the depth direction in a depth range determined based on the layer boundaries. The layer boundary acquisition processing is not indispensable and can be skipped in a case in which, for example, only the generation of three-dimensional motion contrast image is performed and the generation of two-dimensional motion contrast image by projection in the depth direction is not performed. The generation unit 101-42 calculates the motion contrast between the tomographic images that are temporally adjacent in the same cluster. In the present exemplary embodiment, a decorrelation value Mxy as the motion contrast is calculated based on formula (1) below.

$$Mxy = 1 - 2 \times \frac{Axy \times Bxy}{Axy^2 + Bxy^2} \quad (1)$$

In formula (1), Axy denotes the amplitude of tomographic image data A at position (x, y) (amplitude of complex number data having undergone FFT processing), and Bxy denotes the amplitude of tomographic data B at the same position (x, y). Further, $0 \leq Mxy \leq 1$, and the greater the difference between the amplitude values is, the closer to 1 the value becomes. The decorrelation calculation processing as in formula (1) is performed between adjacent tomographic images (that belong to the same cluster), and an image having as a pixel value the mean value of n (n=the number of tomographic images per cluster−1) pieces of obtained motion contrast values is generated as a final motion contrast image.

While the motion contrast is calculated based on the amplitude of complex number data having undergone FFT processing in the present exemplary embodiment, a motion contrast calculation method is not limited to the above-described method. For example, the motion contrast may be calculated based on phase information about the complex number data or based on both amplitude information and phase information. Alternatively, the motion contrast may be calculated based on the real part or the imaginary part of the complex number data.

Further, while the decorrelation value is calculated as the motion contrast in the present exemplary embodiment, the motion contrast calculation method is not limited to the above-described method. For example, the motion contrast may be calculated based on the difference between two values or based on the ratio between two values.

Further, in the above description, the final motion contrast image is obtained by calculating the mean value of the plurality of acquired decorrelation values, the present disclosure is not limited thereto. For example, an image having as a pixel value the median value or maximum value of the plurality of acquired decorrelation values may be generated as the final motion contrast image.

<Step S306>

The display control unit 101-05 displays the motion contrast image generated in step S305 and progress information about the repeat OCTA imaging, on the display unit 104.

Figure 6A:
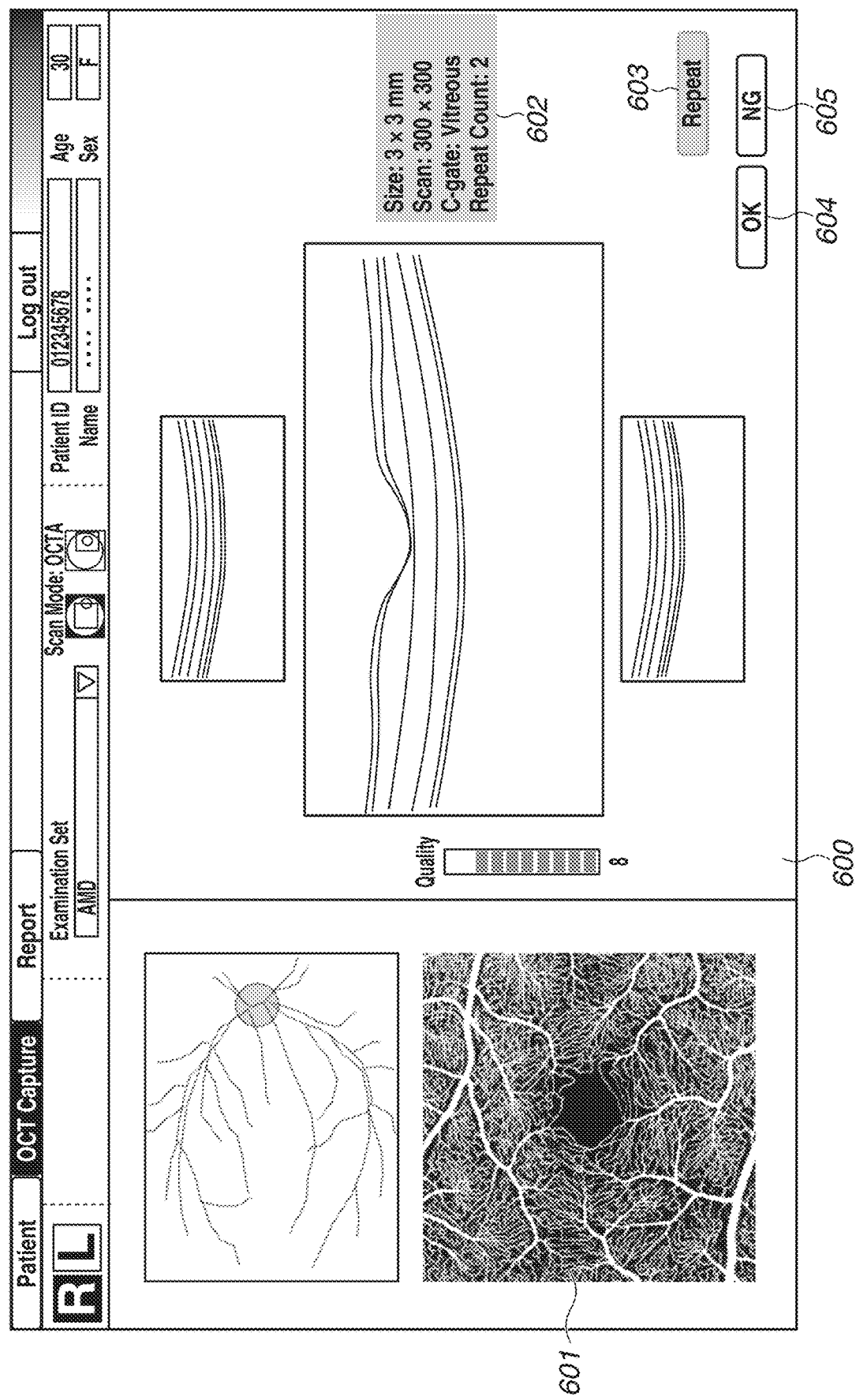
FIGS. 6A to 6E are diagrams each illustrating an example of an imaging check screen displayed on the display unit in step S306 according to the first exemplary embodiment.

FIG. 6A illustrates an example of an imaging check screen 600. In the present exemplary embodiment, an SLO image and a tomographic image, a motion contrast image 601 generated in step S305, and an OCTA imaging repeat count 602 as progress information are displayed on the imaging check screen 600. FIG. 6A illustrates an example of a screen displayed after the second motion contrast image generation.

That is a screen displayed after a motion contrast image is generated again when the repeat-imaging-continue button 603 is selected after the first motion contrast image generation. In the example illustrated in FIG. 6A, the information "Repeat Count: 2" which indicates the number of times the imaging is finished is displayed. In the first imaging, "Repeat Count" does not have to be displayed. In other words, "Repeat Count" may be displayed for the first time on the imaging check screen displayed after the repeat-imaging-continue button 603 is selected. The character string to be displayed is not limited to "Repeat Count", and simply "Repeat" may be displayed. The display control unit 101-05 which displays FIG. 6A on the display unit 104 corresponds to an example of a display control unit configured to display, on a display unit, the first three-dimensional motion contrast image and an interface configured to receive an instruction for acquiring a second three-dimensional motion contrast image of the target eye which is an image captured with a fixation target position the same as a fixation target position used in capturing the first three-dimensional motion contrast image and is to be combined with the first three-dimensional motion contrast image.

While the motion contrast image is displayed as a two-dimensional image in FIG. 6A, the motion contrast image is not limited to the two-dimensional image, and a three-dimensional motion contrast image may be displayed on the imaging check screen 600.

Further, the progress information in the present exemplary embodiment is not limited to the OCTA imaging repeat count at the time point of imaging check. For example, the progress information may be the number of pieces of acquired motion contrast data (the number of acquired tomographic images−1) or the number of acquired tomographic images at the time point of imaging check. Alternatively, the progress information may be the number of tomographic images each having an evaluation value greater than or equal to a predetermined value or the number of pieces of motion contrast data each having an evaluation value greater than or equal to the predetermined value.

Figure 6B:
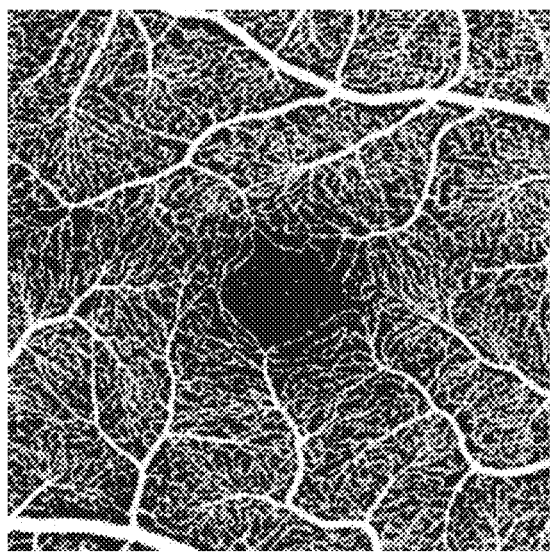
Figure 6C:
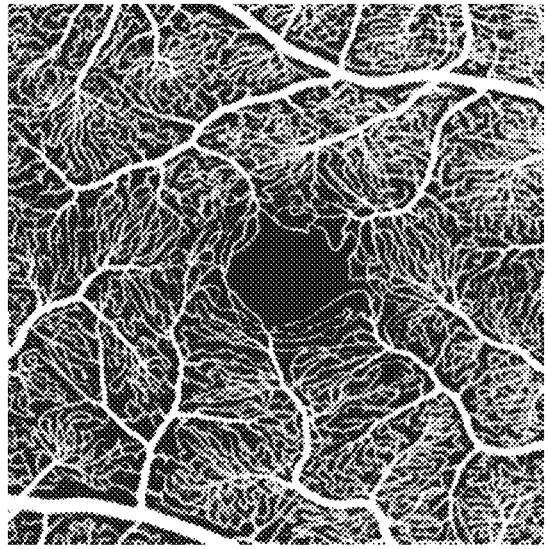

Further, a combined image of motion contrast images acquired before the time point of imaging check may be displayed as the progress information other than numerical values. The display control unit 101-05 may display, for example, a combined image of motion contrast images as the motion contrast image 601. In the case of displaying the combined image of motion contrast images as the motion contrast image 601, processing in steps S313 and S314 described below are executed between steps S305 and S306. Further, the combined image of motion contrast images and the latest imaged motion contrast image (motion contrast image before being combined) may be displayed in a juxtaposed manner. In the present exemplary embodiment, an averaged image of motion contrast images is generated as a combined image. The present exemplary embodiment is not limited to the averaging, and an image acquired by combining a plurality of images of substantially the same position as the imaging position using any method may be displayed. FIGS. 6B and 6C illustrate examples of "the combined image of acquired motion contrast images at the time point of imaging check" which is displayed respectively when the OCTA imaging repeat count N=1 and when N=9. It is found that as the OCTA imaging repeat count increases (as N increases), the image quality improves, and the contrast between regions with vessels and regions without vessels and the continuity of vessels improve, and variations in luminance in the regions without vessels are reduced. The operator can visually check whether the combined image satisfies the target image quality and can issue an instruction to continue or end the repeat OCTA imaging based on the result of visual check. While the combined motion contrast image displayed on the imaging check screen 600 in step S306 is a two-dimensional image, the combined motion contrast image is not limited to the two-dimensional image, and a three-dimensional combined motion contrast image may be displayed on the imaging check screen 600.

Alternatively, an evaluation value calculated for the acquired motion contrast image or the combined image may be displayed as the progress information. In the present exemplary embodiment, the mean value of motion contrast values is calculated as the evaluation value. The progress information is not limited thereto, and other statistical values (e.g., median value, maximum value) of motion contrast values may be calculated and displayed as the progress information. Alternatively, the SN ratio (flow signal-to-noise ratio (fSNR)) of motion contrast values in the macular defined by formula (2) may be calculated and displayed.

$$fSNR = (A_{parafoveal} - A_{faz})/(\sigma_{faz}) \quad (2)$$

In formula (2), Aparafovea denotes the mean value of motion contrast values in the parafoveal region, and Afaz denotes the mean value of motion contrast values in the foveal avascular zone (FAZ). Further, ofaz denotes the standard deviation of motion contrast values in the FAZ. As the image quality improves, the value of the denominator of formula (2) decreases while the value of the numerator of formula (2) increases.

Further, the repeat-imaging-continue button 603 and an OK instruction button 604 and an NG instruction button 605 for the cluster tomographic image and the motion contrast image 601 acquired in steps S304 and S305 are placed at the lower right of the imaging check screen 600.

Figure 6D:
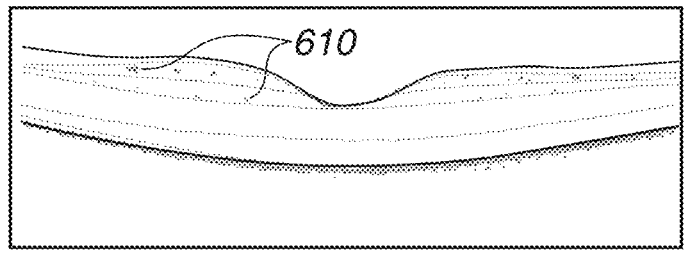

As illustrated in FIG. 6D, a motion contrast 610 at the scan position may be displayed in an overlapping manner on the tomographic image in the imaging check screen 600.

As described above, the display control unit 101-05 displays, on the display unit 104 as the progress information, at least one of a repeat count, a total number of images acquired by repeat imaging, the number of images each having an evaluation value greater than or equal to the predetermined value among the images acquired by repeat imaging, evaluation data on the acquired image, and a combined image of the acquired motion contrast image.

<Step S307>

The operator determines whether to continue the OCTA imaging based on the progress information displayed on the imaging check screen 600. More specifically, the operator determines whether the repeat count reaches a desired repeat count, whether the combined image satisfies the desired image quality, or the like and then determines whether to continue the repeat imaging. If the repeat OCTA imaging is to be continued (YES in step S307), the processing proceeds to step S308. On the other hand, if the repeat OCTA imaging is not to be continued (NO in step S307), the processing proceeds to step S310.

<Step S308>

Upon pressing the repeat-imaging-continue button 603 on the imaging check screen 600 by the operator, the information processing apparatus 101 instructs the tomographic imaging apparatus 100 to continue the OCTA imaging.

Any type of a user interface may be used as the user interface for issuing an instruction to continue the repeat imaging. Besides the normal buttons illustrated in FIG. 6A, for example, a toggle button, a radio button, a checkbox, a list box, a context menu, or the like can be used.

<Step S309>

In the N-th OCTA imaging, the information processing apparatus 101 saves:

a) an acquired image group (SLO image, tomographic image) and imaging condition data on the image group, and an evaluation value (Quality Index) of each image belonging to the image group, b) a generated motion contrast image and generation condition data on the motion contrast image, and c) attribute data on a motion contrast image group acquired up to the N-th OCTA imaging, on the external storage unit 102 in association with the examination time/date and information that identifies the target eye.

As the generation condition data on the motion contrast image, b-1) the same data as the attribute data of the tomographic image (scan region size, the number of pixels, the number of tomographic images per cluster), b-2) the data specific to the motion contrast image (as to whether projection artifact removal processing is performed or not), b-3) the data specific to the two-dimensional motion contrast image (projection depth range, projection method (e.g., MIP, AIP), display condition (e.g., tone curve setting)), and b-4) the data specific to the three-dimensional motion contrast image (rendering method, display condition (e.g., tone curve setting)) are saved. The data b-1) may be saved as a link to the saved imaging condition data a).

Further, the information processing apparatus 101 associates the plurality of motion contrast images acquired by the repeat OCTA imaging as a motion contrast image group and saves attribute data on the group in the external storage unit 102.

In the present exemplary embodiment, c-1) a motion contrast image group name assigned to the motion contrast image group acquired by the repeat OCTA imaging, c-2) a path to motion contrast image data belonging to the motion contrast image group indicated by the motion contrast image group name c-1), c-3) the evaluation values of the motion contrast images included in the list c-2), and c-4) a path to a reference image for use in aligning the images included in the list c-2) are saved on the external storage unit 102 as attribute data on the motion contrast image group.

The attribute data c) on the motion contrast image group may be generated in the first OCTA imaging (N=1), and when N≥2, the attribute data generated when N=1 may be referred to and data can be added or the attribute data can be updated. Further, the attribute data c) is not limited to a character string and may be, for example, a numerical value such as an identification number. If the image saving and associating processing is completed, the processing returns to step S304 to continue the repeat OCTA imaging.

<Step S310>

The operator determines whether to save the acquired motion contrast image 601 based on the motion contrast image 601 acquired in the N-th OCTA imaging of the repeat count N and displayed on the imaging check screen 600. If the acquired motion contrast image 601 is to be saved (YES in step S310), the processing proceeds to step S311. On the other hand, if the acquired motion contrast image 601 is not to be saved (NO in step S310), the processing proceeds to step S312.

<Step S311>

Upon pressing the button 604 on the imaging check screen 600 by the operator:

1) the information processing apparatus 101 instructs the tomographic imaging apparatus 100 to end the repeat OCTA imaging, and 2) an instruction to save the acquired motion contrast image is given to the information processing apparatus 101.

<Step S312>

Upon pressing the button 605 on the imaging check screen 600 by the operator, the information processing apparatus 101 instructs the tomographic imaging apparatus 100 to end the repeat OCTA imaging. In this case, the acquired motion contrast image is not saved.

While a case in which the saving and associating processing is not performed on the image acquired in the N-th OCTA imaging if an instruction-to-disapprove is input is described in the present exemplary embodiment, it is not limited thereto. For example, if an instruction-to-disapprove is input, information (e.g., NG label) indicating that the image is not suitable for observation or analysis may be added to the image acquired in the N-th OCTA imaging and then the image with the information may be saved and associated.

<Step S313>

The information processing apparatus 101 performs saving and associating processing on the acquired motion contrast image 601. Details of the image saving and associating processing are similar to those in step S309, so that detailed description thereof is omitted.

<Step S314>

The image processing unit 101-04 aligns the motion contrast images in a group acquired through the repeat OCTA imaging and averages the motion contrast images to generate a combined motion contrast image. The combining processing is not limited to the simple averaging. For example, a value obtained by weighting and averaging the luminance values of the motion contrast images may be used, or a statistical value such as a median value may be calculated.

Further, the judgement unit 101-431 may judge whether an unsuitable motion contrast image for the combining processing is included, and then the combining unit 101-43 may perform combining processing excluding the motion contrast image judged unsuitable. For example, the judgement unit 101-431 may judge a motion contrast image unsuitable for the combining processing if the evaluation value (statistical value relating to the decorrelation value, fSNR) calculated for each motion contrast image in step S306 is outside a predetermined range.

While the combined motion contrast image is generated as a two-dimensional image in the present exemplary embodiment, the layer boundary acquisition processing by the image feature acquisition unit 101-44 and the projection processing by the projection unit 101-45 may be skipped in a case of generating the combined motion contrast image as a three-dimensional image. Further, the depth range is not limited to a single depth range, and a plurality of two-dimensional combined motion contrast images may be generated in each of different depth ranges.

Further, the image processing unit 101-04 also generates:

a') the images (tomographic images) used to generate the combined motion contrast image, imaging condition data on the images, and a link to evaluation value data on the images, b') the combined motion contrast image and combining condition data on the combined motion contrast image, and evaluation value data on the combined image, and c) attribute data on the motion contrast image group, for the generated combined motion contrast image as in the case of step S309 or S313.

The combining condition data b') on the combined motion contrast image includes b'-1) the same data as the attribute data on the tomographic image, b'-2) the data specific to the combined motion contrast image, b'-3) the data specific to the two-dimensional combined motion contrast image, and b'-4) the data specific to the three-dimensional combined motion contrast image.

Further, in a case of the combined motion contrast image, not only the data "as to whether projection artifact removal processing is performed or not" but also b'-2-1) a path to the reference image in the image alignment performed in the combining processing (the path is actually a link to the data c-4) saved as the attribute data on the motion contrast image group), b'-2-2) the weight by which each motion contrast image corresponding to the path included in the list c-2) is multiplied in the combining processing (if the motion contrast image is not to be used in the combining, the weight is zero), and b'-2-3) the number of motion contrast images each having a weight greater than zero (a list of repeat counts (N) in a case in which the weight >0) are also saved as the data b'-2) specific to the combined motion contrast image.

The image processing unit 101-04 saves the generated combined motion contrast image, and data belonging to the data a'), the data b'), and the data c) described in the description of step S314, on the external storage unit 102.

<Step S315>

The tomographic imaging apparatus 100 ends the OCTA imaging based on the instruction received from the information processing apparatus 101.

<Step S316>

Figure 8A:
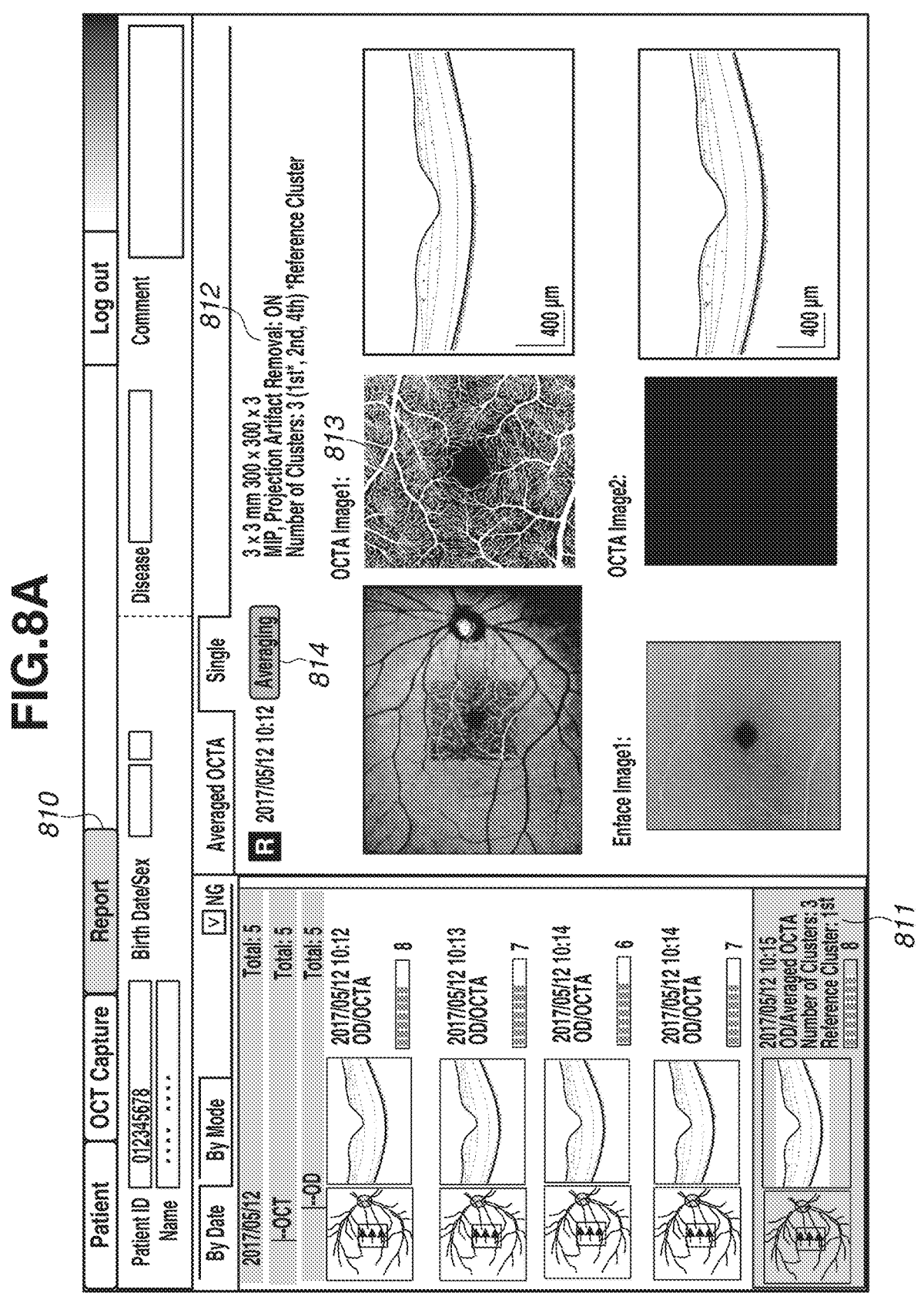

As illustrated in FIG. 8A, the display control unit 101-05 displays a report screen 810 on the display unit 104.

The report screen 810 displays a combined motion contrast image 813 and information 812 about the combining condition of the combined motion contrast image, and this corresponds to b') the combined motion contrast image and the combining condition data on the combined motion contrast image, and the evaluation value data on the combined image, which are generated by the image processing unit 101-04 in step S314.

In FIG. 8A, b'-1) the same data as the attribute data of the tomographic image (scan region size (3×3 mm), the number of pixels (300×300), the number of tomographic images per cluster (×3)), b'-2) the data specific to the combined motion contrast image (the data as to whether projection artifact removal processing is performed or not (Projection Artifact Removal: ON), the reference image in the image alignment performed in the combining processing (1st*, i.e., the image of the first repeat imaging), the number of motion contrast images with the weight in the combining processing >0 (Number of Clusters: 3)), and b'-3) the data specific to the two-dimensional combined motion contrast image (projection method (MIP))

are displayed on the report screen 810 as the information 812 about the combining condition. In the example illustrated in FIG. 8A, it is indicated that the image is a combined image of the motion contrast images captured in the first imaging, the second imaging, and the fourth imaging. Alternatively, the evaluation values of the image quality of the motion contrast images used in the combining may be displayed. More specifically, in the displaying of the combined image generated by the combining unit, the display control unit 101-05 displays, on the display unit as combining condition information, at least one of the repeat count, a number of images used in the combining, a reference image in the combining, a numerical value of an image that indicates a number of times the imaging is performed when the image is acquired, an imaging condition of the image used in the combining, and an evaluation value for the image used in the combining.

Further, an examination image list includes an item 811 regarding the combined image, and the item 811 also displays information (Number of Clusters: 3, Reference Cluster: 1st) about the combining condition to facilitate examination image selection even in a case of generating the combined image under different combining conditions.

The combining condition data to be displayed on the report screen 810 is not limited to the above-described combining condition data.

For example, as illustrated in FIG. 8B, the number of pieces of motion contrast data used to generate the combined motion contrast image (Number of MC images; (the number of tomographic images per cluster−1) x the number of motion contrast images used in the combining) may be displayed as the combining condition.

Alternatively, as illustrated in FIG. 8C, the number of tomographic images used to generate the combined motion contrast image (Number of B-scans; the number of tomographic images per cluster×the number of motion contrast images used in the combining) may be displayed as the combining condition.

Alternatively, as illustrated in FIG. 8D, evaluation value data (QI) on the tomographic images or motion contrast images used in the combining processing may be displayed.

Alternatively, as illustrated in FIG. 8E, information (ref=composite) that indicates that the reference image used in the registration for the combining is generated by combining predetermined motion contrast images may be displayed.

While the two-dimensional combined motion contrast image is displayed in the present exemplary embodiment, the present exemplary embodiment is not limited thereto, and a three-dimensional combined motion contrast image may be displayed on the report screen 810.

Figure 6E:
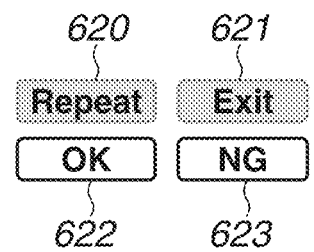
Figure 7:
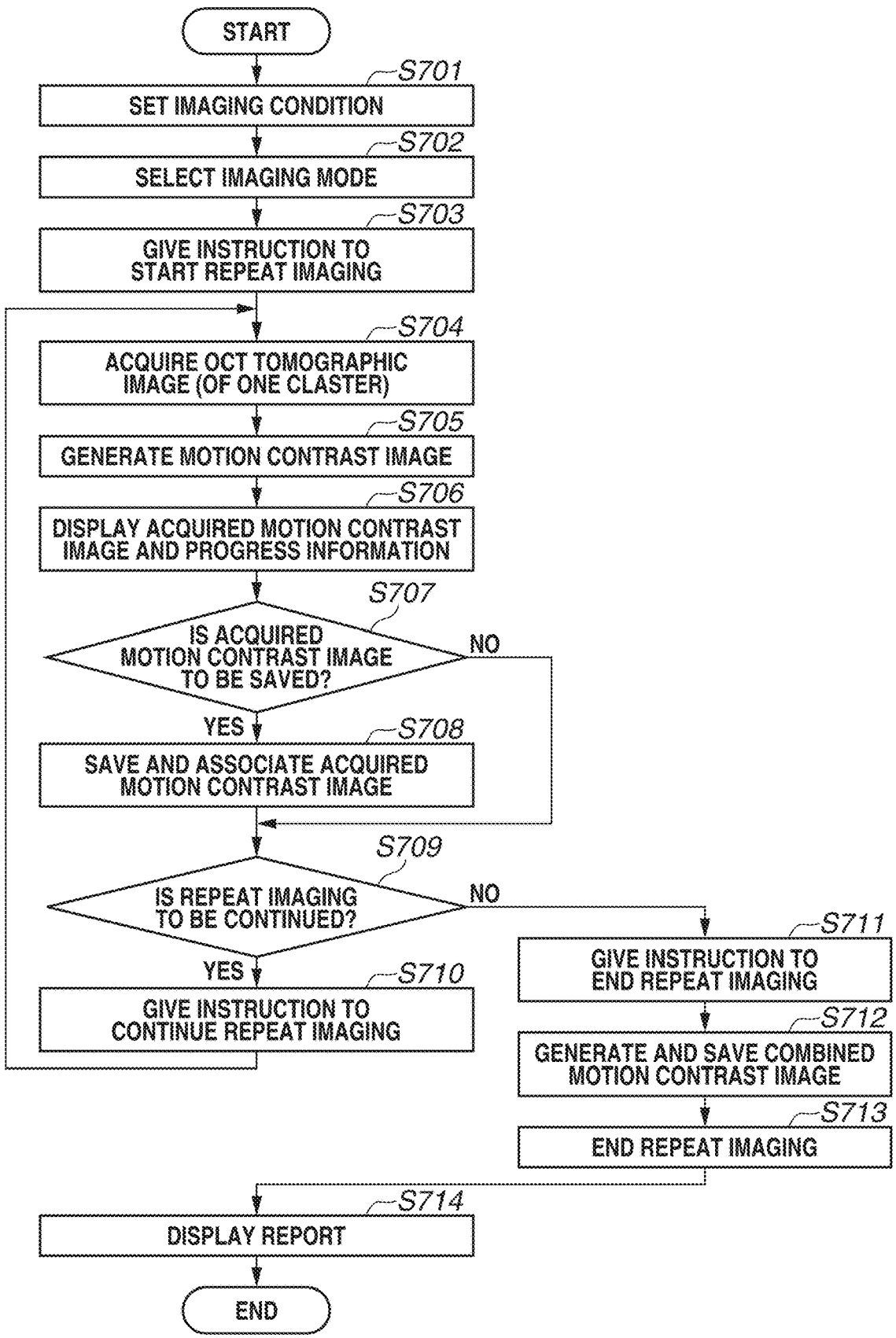
FIG. 7 is a flowchart illustrating an example of processing executable by the information processing system according to the first exemplary embodiment.

The scope of the present disclosure also encompasses a case in which a user interface for selecting whether to continue the repeat OCTA imaging and a user interface for selecting whether to save data acquired in the N-th OCTA imaging are displayed as different user interfaces on the imaging check screen. As an example, FIG. 7 illustrates a processing flow for displaying, on the imaging check screen 600, the user interface illustrated in FIG. 6E. In step S707, the operator determines whether data acquired in the N-th OCTA imaging is to be saved (or whether an unsuitable label is to be added). If the data is to be saved (YES in step S707), the operator presses an instruction-to-accept button 622, and in step S708, saving and associating processing is performed. On the other hand, if the data is not to be saved (or if the unsuitable label is to be added to the data and then the data is saved) (NO in step S707), the operator presses a not-accept button 623, and the processing proceeds to step S709.

Next, in step S709, the operator determines whether to continue the repeat OCTA imaging. If the repeat OCTA imaging is to be continued (YES in step S709), then in step S710, the operator presses a repeat-imaging-continue button 620, and the processing proceeds to step S704. On the other hand, if the repeat OCTA imaging is not to be continued (NO in step S709), then in step S711, the operator presses an end-repeat-imaging button 621, and the processing proceeds to step S712.

In step S712, the combining unit 101-43 combines, for example, the motion contrast images saved in step S708.

Figure 9:
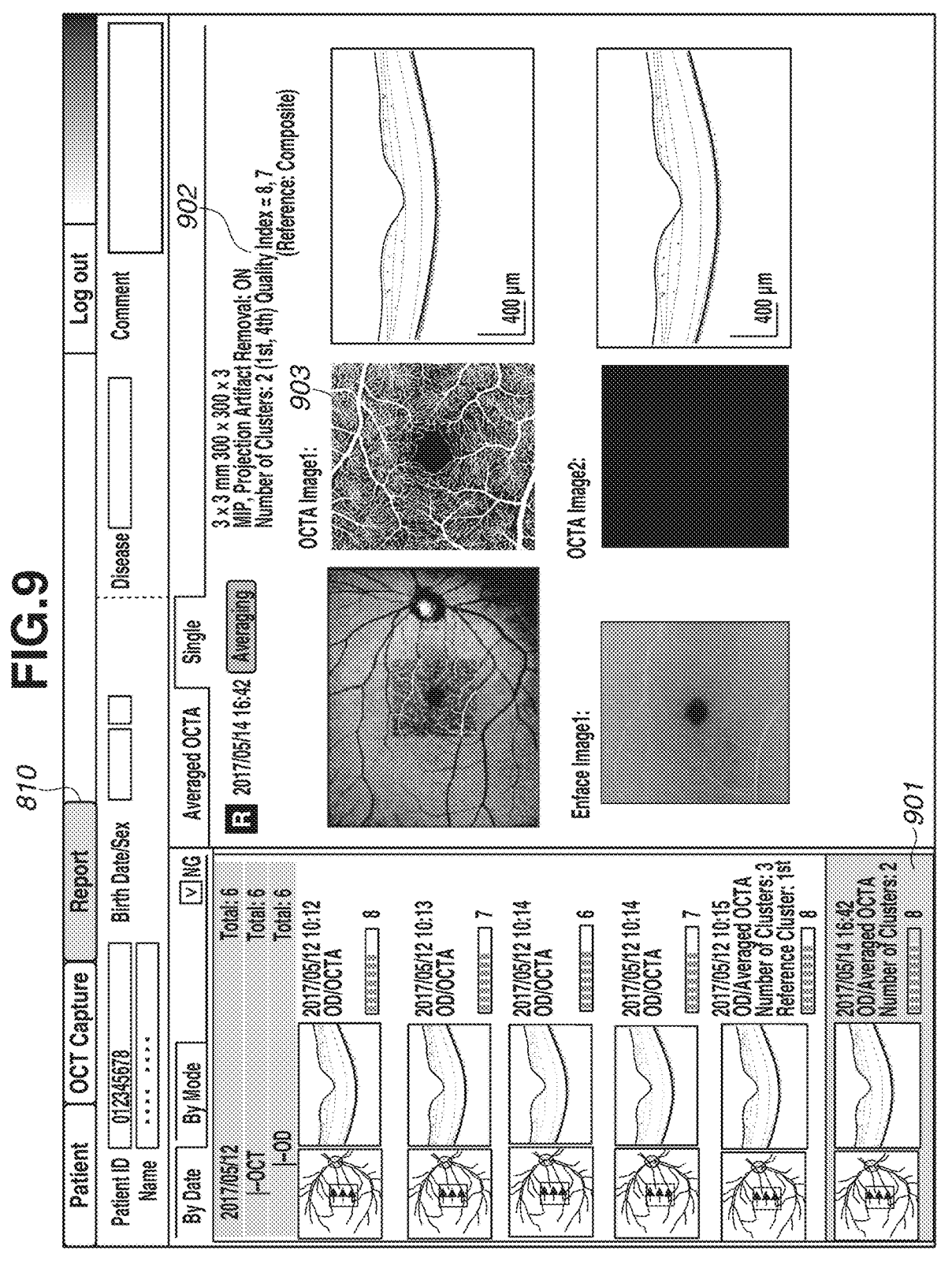

Further, while the case in which the combining unit 101-43 generates the combined motion contrast image based on the instruction to end the repeat OCTA imaging is described in the present exemplary embodiment, the procedure of generating a combined motion contrast image is not limited thereto. For example, a combined-motion-contrast-image generation button 814 is provided on the report screen 810 in FIG. 8A. Then, the information processing apparatus 101 may be configured in such a manner that the combining unit 101-43 generates a combined motion contrast image if the operator explicitly presses the combined-motion-contrast-image generation button 814 after the OCTA imaging is completed (this can be a date after the imaging date). In the case in which the operator explicitly presses the combined-motion-contrast-image generation button 814 to generate a combined image, a combined motion contrast image 903 and combining condition data 902 are displayed on the report screen 810, and an item 901 about the combined image is displayed on the examination image list, as illustrated in FIG. 9. While the combined image generation time/date is displayed in FIG. 9, for example, the imaging time/date may be displayed, or the imaging time/date and the combining time/date may both be displayed on the report screen 810.

Further, in a case in which the operator presses the combined-motion-contrast-image generation button 814, the display control unit 101-05 performs the following processing. Specifically, a target image selection window 820 for combining illustrated in FIG. 8F is displayed, and if the operator operates the input unit 103 to designate combination target images 821 and presses an OK button 823, the combining unit 101-43 generates a combined motion contrast image and displays the generated combined motion contrast image on the display unit 104. The scope of the present disclosure also encompasses a case in which a previously-generated combined motion contrast image 822 is selected and combined. Further, in a case of generating a two-dimensional combined image, the operator designates a projection depth range and then presses the combined-motion-contrast-image generation button 814. To designate the projection depth range, the operator may designate the type of a retinal layer boundary line and an offset position on the report screen 810 or may select a depth range from an existing depth range set displayed in a list box. Further, in a case in which the operator presses the projection depth range and the combined-motion-contrast-image generation button 814, two-dimensional images generated by projecting a three-dimensional motion contrast image may be combined to generate a two-dimensional combined image, or after a three-dimensional combined image is generated, a two-dimensional combined image may be generated by projecting the three-dimensional combined image.

Alternatively, a combined image may be generated before the combined-motion-contrast-image generation button 814 is selected, and the display control unit 101-05 may display a predetermined motion contrast image to be combined on the display unit 104 as a default image, and may switch to the combined image when the combined-motion-contrast-image generation button 814 is selected.

According to the above-described configuration, the information processing apparatus 101 issues an instruction to continue or not continue the repeat imaging by the operator pressing the repeat imaging button based on the progress information displayed on the imaging check screen. In response to the instruction, motion contrast images to be used to generate a desired high-contrast combined motion contrast image are acquired.

In this way, motion contrast data necessary to acquire a desired high-contrast combined motion contrast image is adequately and promptly acquired.

Now a second exemplary embodiment will be described. An information processing apparatus according to the second exemplary embodiment presets a target value for OCTA imaging at the time of setting the imaging condition (setting of imaging condition (B)) and automatically executes repeat OCTA imaging until the target value is reached.

Figure 10:
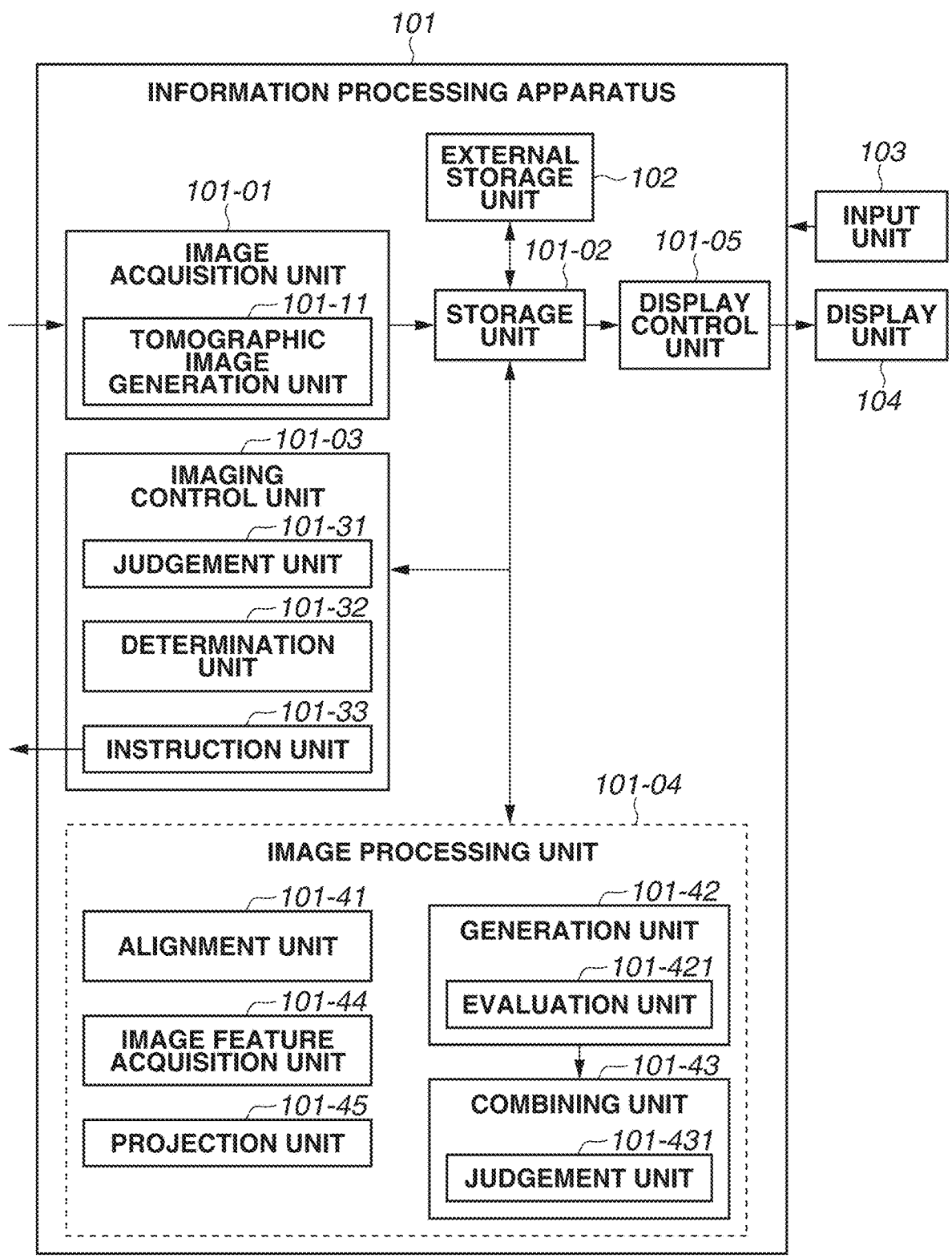
FIG. 10 is a block diagram illustrating an example of a configuration of an information processing apparatus according to a second exemplary embodiment.
Figure 11:
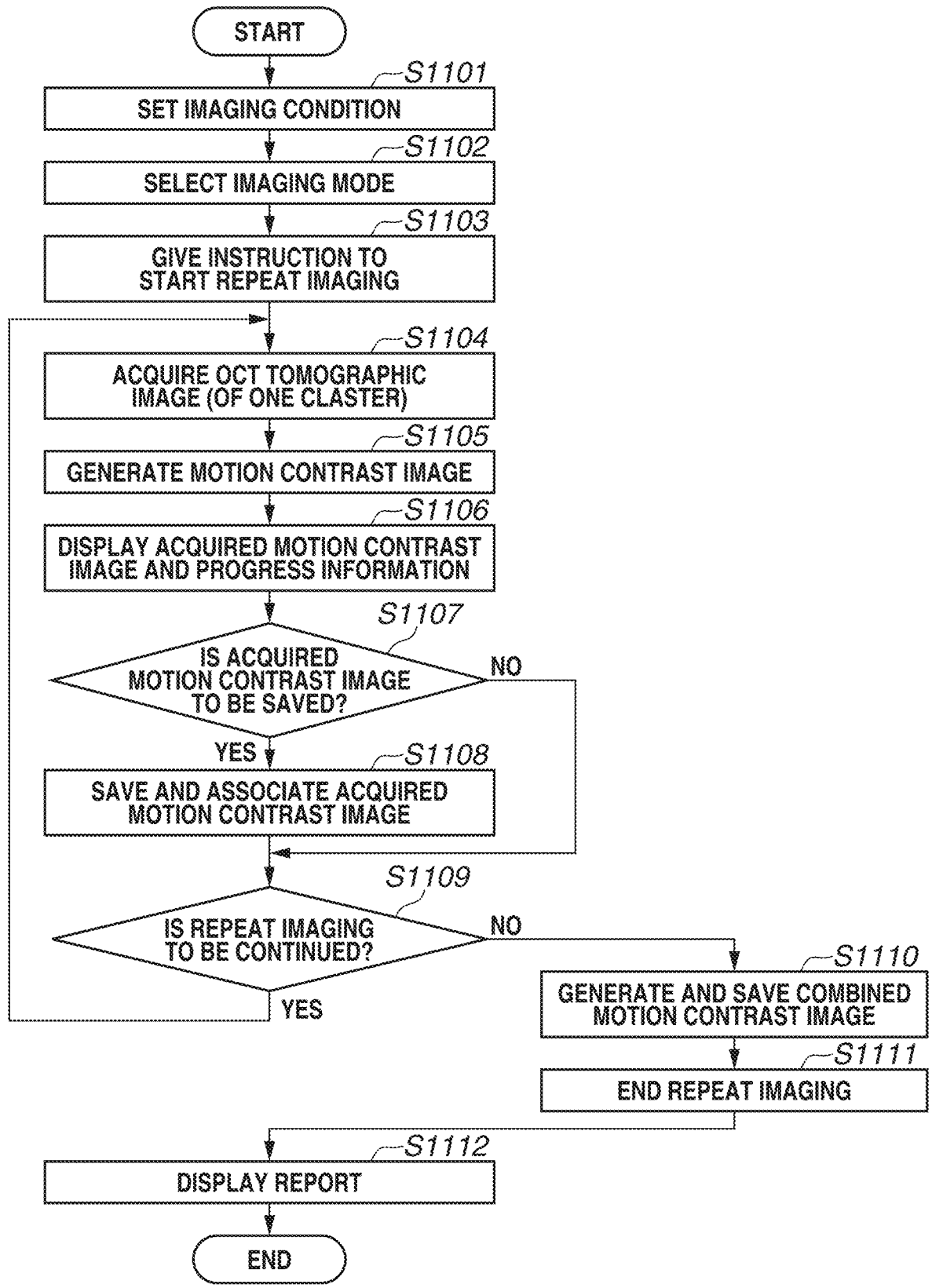
FIG. 11 is a flowchart illustrating an example of processing executed by an information processing system according to the second exemplary embodiment.

FIG. 10 illustrates a configuration of the information processing system 10 including the information processing apparatus 101 according to the present exemplary embodiment. The present exemplary embodiment is different from the first exemplary embodiment in that the imaging control unit 101-03 includes a judgement unit 101-31, a determination unit 101-32, and an instruction unit 101-33. Further, an image processing flow is as illustrated in FIG. 11, and steps other than steps S1101, S1106, and S1109 are similar to those in the first exemplary embodiment, so that description thereof is omitted.

<Step 1101>

The operator operates the input unit 103 to set the imaging condition of OCTA images to the tomographic imaging apparatus 100.

Figure 12A:
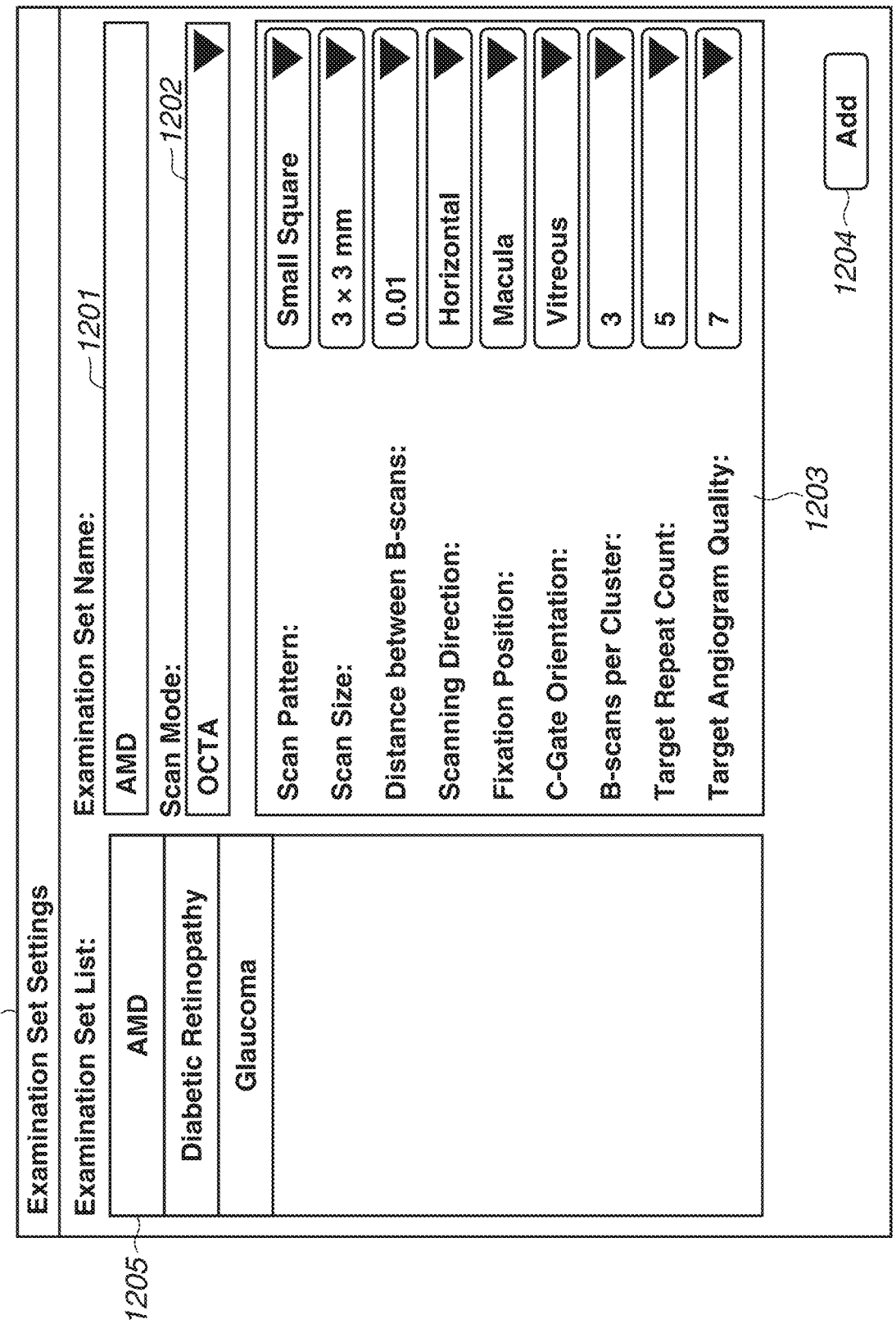
FIGS. 12A and 12B are diagrams illustrating an example of an imaging condition setting screen and an imaging check screen displayed on a display unit according to the second exemplary embodiment.

FIG. 12A illustrates an examination set setting screen 1200 displayed on the display unit 104, and an imaging parameter designation section 1203 is different from the first exemplary embodiment. In the present exemplary embodiment, the imaging condition (A) "for individual OCTA imaging and the imaging condition" (B) "for the entire repeat OCTA imaging" are both input into the imaging parameter designation section 1203, and as the imaging condition (B), an instruction about B-1) a target value for the repeat count (Target Repeat Count), and B-2) a target value for the image quality of a averaged OCTA image (Target Angiogram Quality)

is given. Alternatively, one of the target value for the repeat count and the target value for the image quality of the averaged OCTA image may be set as the imaging condition. The present exemplary embodiment is not limited thereto, and an instruction for any imaging parameter for repeat imaging may be given. For example, an instruction about B-3) a target value for a total value of the number of motion contrast images to be acquired (in the case of FIG. 12A, 2×5=10), and B-4) a target value for a total value of the number of OCT tomographic images (in the case of FIG. 12A, 3×5=15)

may be given. Further, the scope of the present disclosure also encompasses the cases in which an instruction about B-3') a target value about the sum of OCT tomographic images that an OCT tomographic image quality index value (Single OCT Quality Index; SOQI) calculated in individual OCTA imaging is greater than or equal to a predetermined value
or
B-4') a target value about the sum of motion contrast images that a motion contrast image quality index value (Single OCTA Quality Index; SAQI) calculated in individual OCTA imaging is greater than or equal to a predetermined value is given.

For example, an instruction to "acquire 15 OCT tomographic images that satisfy SOQI≥7" may be given as the imaging condition, as it is an index value that SOQI is calculable in the range of 0 to 10. Further, while any index value may be calculated as SOQI, the mean value of the decorrelation value calculated for the motion contrast images is determined in the present exemplary embodiment and, for example, an instruction to "acquire 10 motion contrast images that satisfy SAQI≥0.1" may be given as the imaging condition.

<Step 1106>

The display control unit 101-05 displays the motion contrast image generated in step S1105 and progress information about the repeat OCTA imaging, on the display unit 104.

Figure 12B:
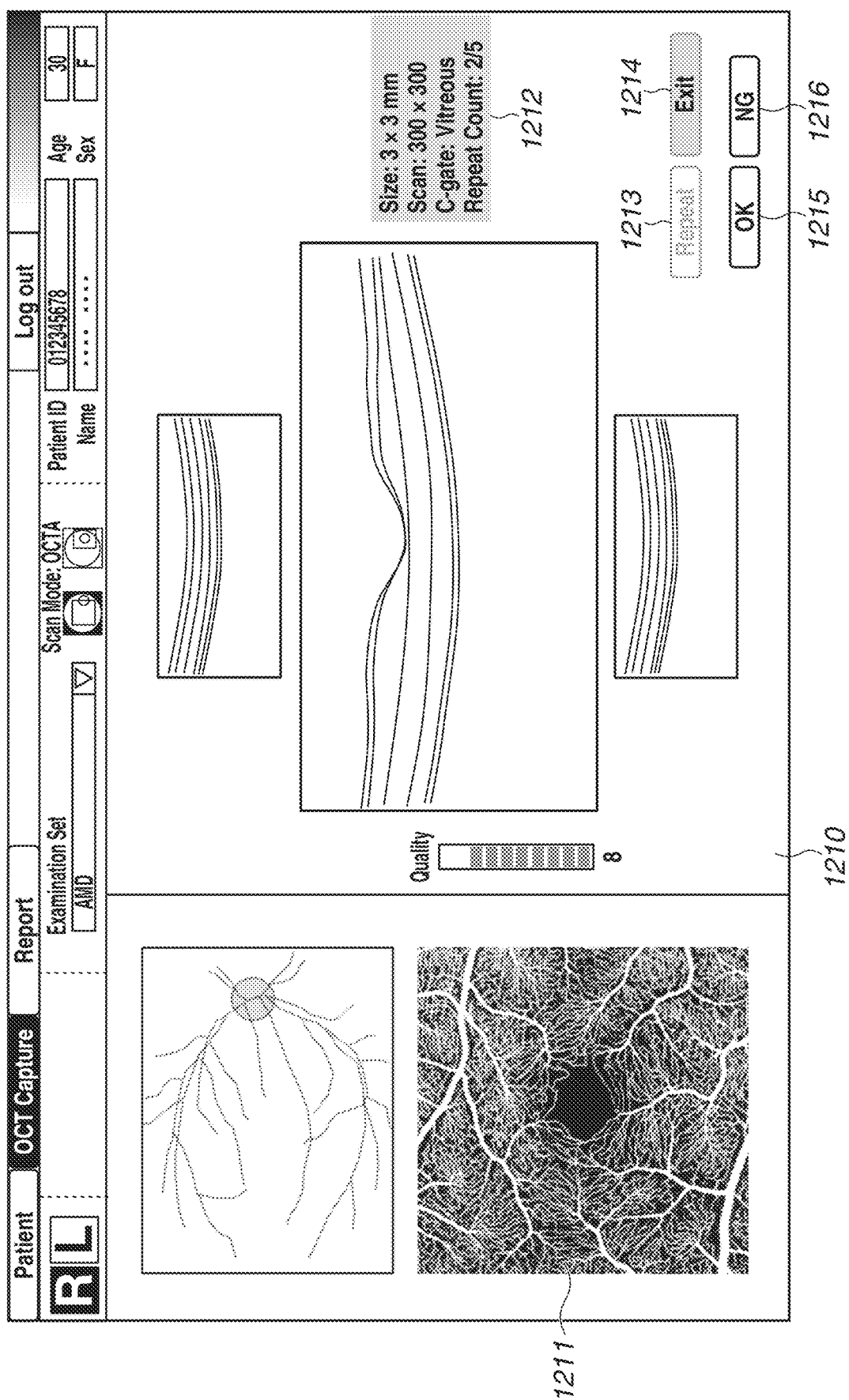

In the present exemplary embodiment, the display control unit 101-05 displays as the progress information the ratio of "the number of times an instruction to image and accept is given up to the time point of imaging check" to "the target repeat count" (the ratio is 2/5 in FIG. 12B), on an imaging check screen 1210. Alternatively, "the target repeat count" can be displayed.

Alternatively, as the progress information, one of
(1) the ratio of "the number of pieces of motion contrast data generated and judged acceptable up to the time point of imaging check" to "the number of pieces of target motion contrast data" and
(2) the ratio of "the evaluation value calculated for the combined motion contrast image generated using the motion contrast image acquired and judged acceptable up to the n-th repeat imaging" to "the target value of the evaluation value of the combined motion contrast image" may be displayed. In other words, the display control unit 101-05 displays at least one of the imaging condition of the acquired image and the number of images judged acceptable, on the display unit 104 as the progress information.

The operator determines whether to save the data acquired in the N-th OCTA imaging. If the acquired data is to be saved (YES in step S1107), the operator presses an OK instruction button 1215 on the imaging check screen 1210, and the processing proceeds to step S1108. In step S1108, the acquired motion contrast image is saved and associated. On the other hand, if the acquired data is not to be saved (NO in step S1107), the operator presses an NG instruction button 1216, and the processing proceeds to step S1109.

<Step 1109>

The imaging control unit 101-03 judges whether the imaging condition (B) among the imaging conditions set in step S1101 reaches the target value set in step S1101. In the present exemplary embodiment, whether the repeat count (Repeat Count) N reaches the target value (5 times) is judged. Alternatively, the imaging control unit 101-03 may judge whether the target value of the averaged OCTA image quality is reached, or whether the condition of the image quality and the condition of the number of times are both satisfied may be set as the judgement condition. If the number of times the OCTA imaging is repeated reaches the target value (NO in step S1109), the processing proceeds to step S1110. On the other hand, if the number of times the OCTA imaging is repeated does not reach the target value (YES in step S1109), the processing proceeds to step S1104. While a repeat-imaging-continue button 1213 on the imaging check screen 1210 is displayed as being selected (pressed) in the present exemplary embodiment, the repeat-imaging-continue button 1213 does not necessarily have to be displayed on the imaging check screen 1210. Further, an end-repeat-OCTA-imaging (Exit) button 1214 is displayed in such a manner that the button 1214 can be pressed to stop the OCTA imaging during the examination in view of the physical condition of the examinee.

According to the above-described configuration, the information processing apparatus 101 automatically repeats OCTA imaging based on the target value for the OCTA imaging that is determined at the time of setting the imaging condition, until the target value is reached.

In this way, motion contrast data necessary to acquire a desired high-contrast combined motion contrast image is promptly acquired.

The information processing apparatus according to a third exemplary embodiment performs repeat OCTA imaging at a different date and time as a follow-up examination of the same target eye under substantially the same imaging conditions.

More specifically, a case will be described below in which the operator determines whether to continue the OCTA imaging based on the target value of the repeat OCTA imaging parameter set in the baseline test selected by the operator and the combining condition data on the combined image generated in the baseline test.

Figure 13:
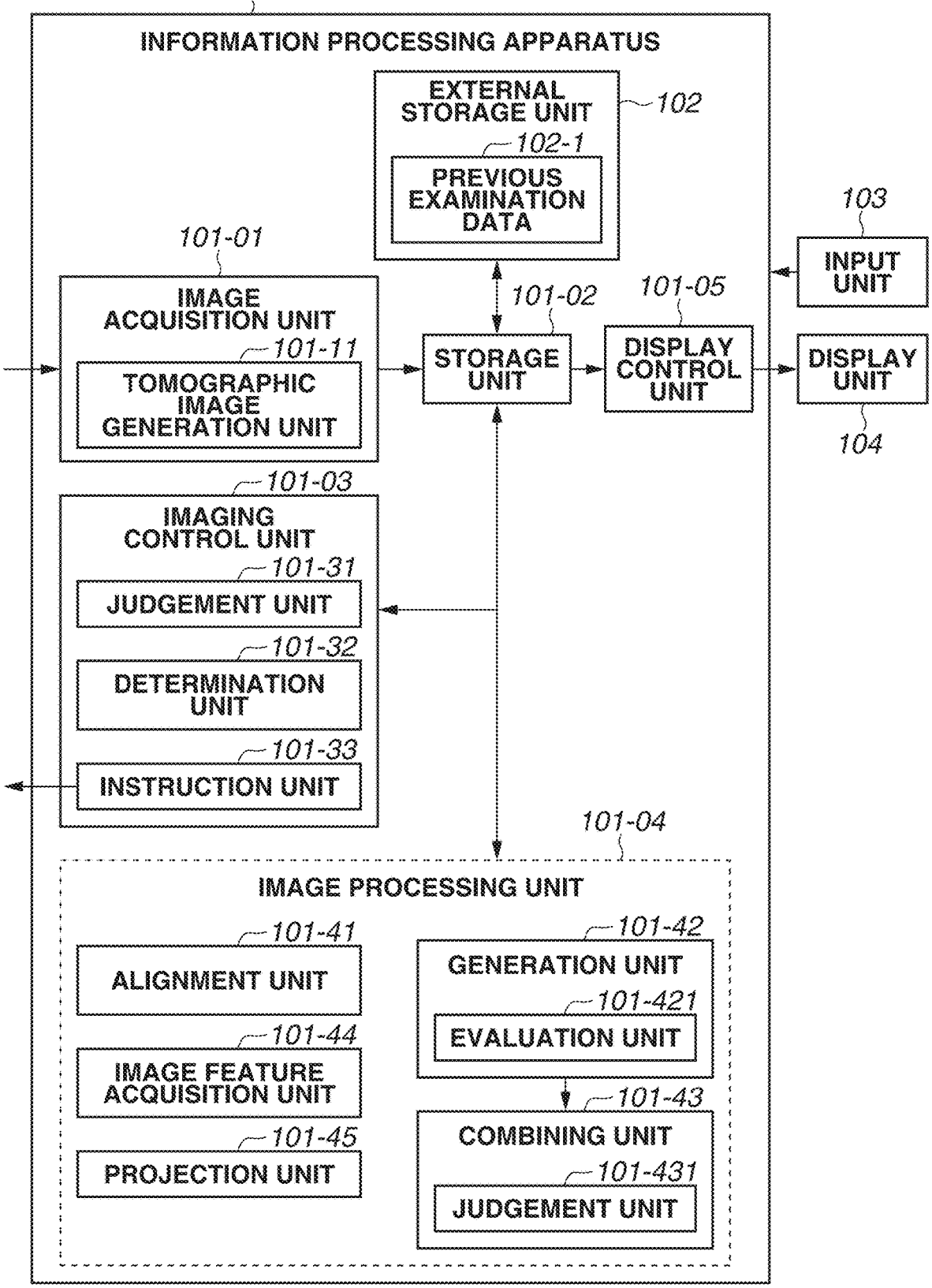
FIG. 13 is a block diagram illustrating an example of a configuration of an information processing apparatus according to a third exemplary embodiment.
Figure 14:
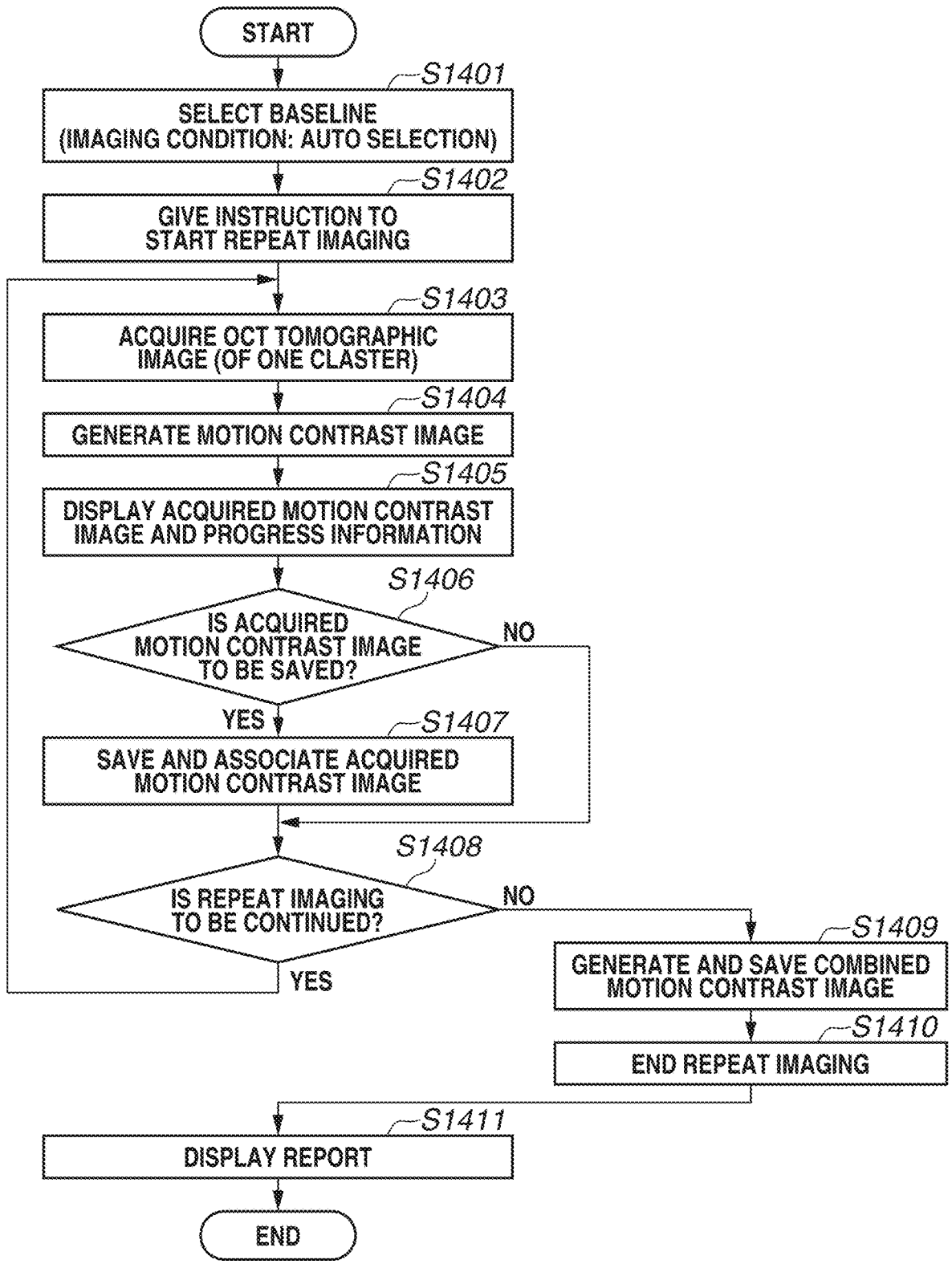
FIG. 14 is a flowchart illustrating an example of processing executed by an information processing system according to the third exemplary embodiment.
Figure 16:
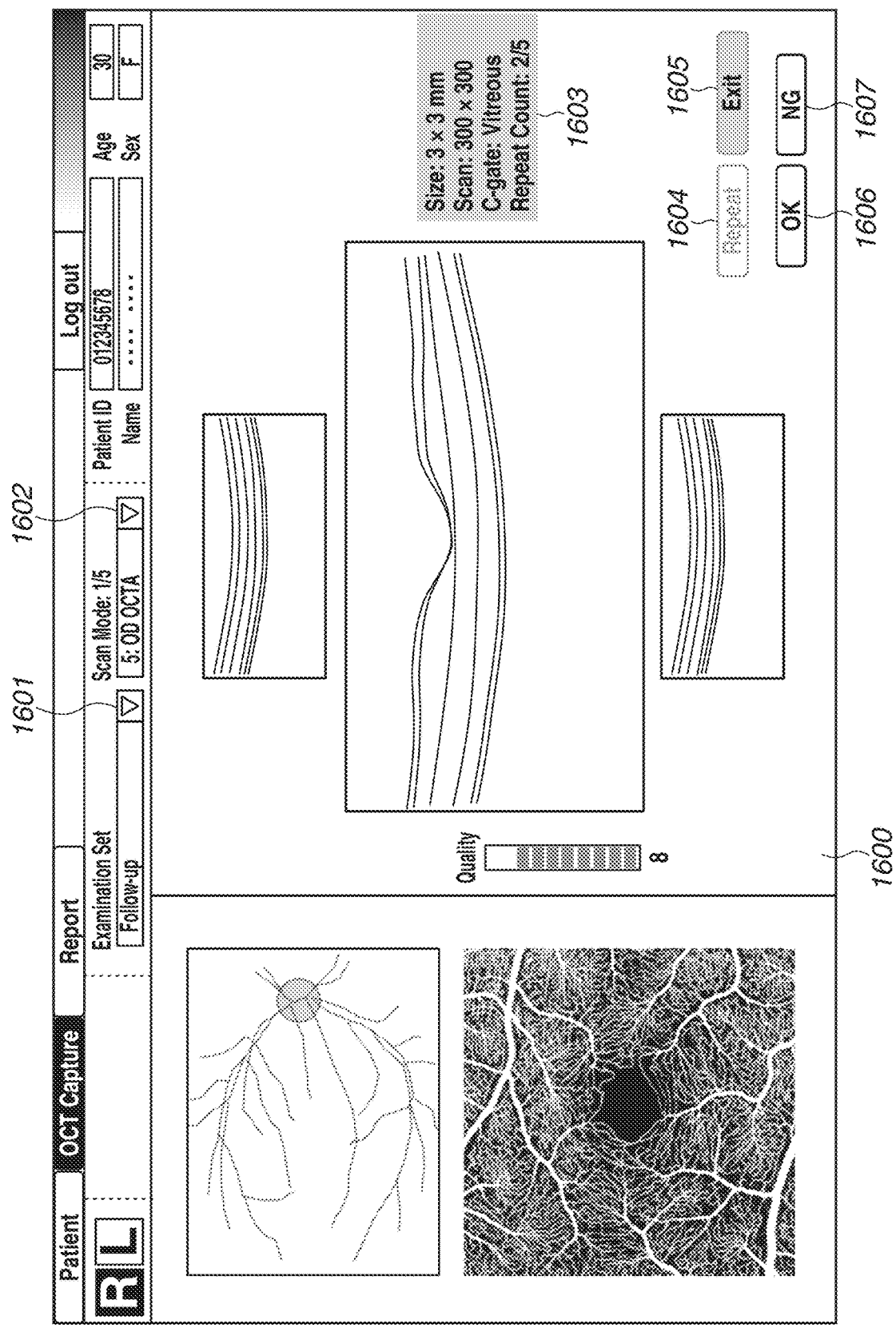
FIG. 16 is a diagram illustrating an example of an imaging check screen displayed on the display unit according to the third exemplary embodiment.

FIG. 13 illustrates a configuration of the information processing system 10 including the information processing apparatus 101 according to the present exemplary embodiment. The present exemplary embodiment is different from the second exemplary embodiment in that the external storage unit 102 includes a previous examination data 102-1. Further, an image processing flow in the present exemplary embodiment is as illustrated in FIG. 14, and steps other than steps S1401 and S1403 are similar to those in the second exemplary embodiment, so that description thereof is omitted.

<Step 1401>

The operator selects a baseline test for the target eye whose previous examination data is saved.

Figure 15A:
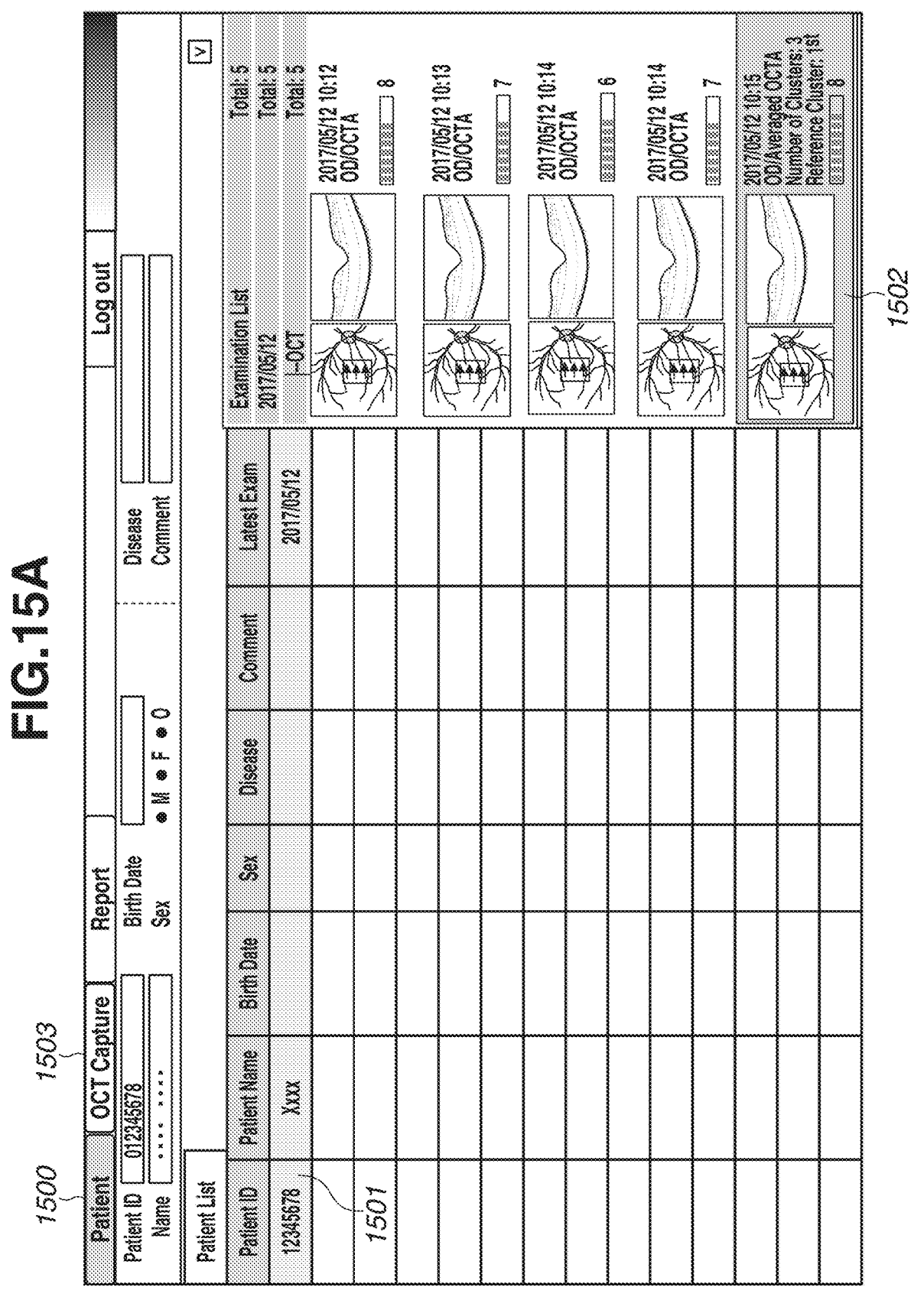

In the present exemplary embodiment, the operator operates the input unit 103 on a patient screen 1500 as illustrated in FIG. 15A to select an examinee 1501 from a patient list (Patient List). Further, the operator selects a baseline test (Baseline) in the follow-up examination from an examination list (Examination List) of the examinee to determine the baseline test. As to the selection of an examination set and a scan mode, the operator opens an imaging screen (OCT Capture) with the baseline test being selected so that the information processing apparatus 101 selects the follow-up examination set and sets the scan mode to the same scan mode as the baseline test. For example, on an imaging screen 1510 illustrated in FIG. 15B, "follow-up" is selected as the examination set and the "OCTA" mode as the scan mode.

Further, the information processing apparatus 101 sets the imaging condition (A) "for individual OCTA imaging and the imaging condition" and (B) "for the entire repeat OCTA imaging" to the same setting values as the imaging conditions of the baseline test. As the imaging condition (B), combining condition data (e.g., evaluation value calculated for the combined image) of the combined image generated in the baseline test may be set as the target value.

<Step 1403>

The imaging control unit 101-03 instructs the tomographic imaging apparatus 100 to perform OCTA imaging (of one cluster in each scan position) based on the imaging condition (same as the baseline test) determined in step S1401, and the tomographic imaging apparatus 100 acquires the corresponding OCT tomographic image.

Instructions to change the right/left eye, fixation target position, and the scan position are not received while repeat OCTA imaging is executed in the follow-up examination.

Further, while repeat OCTA imaging is executed in the follow-up examination, the imaging control unit 101-03 performs tracking processing and imaging position determination using the same image as the SLO image (front image) acquired in the baseline test selected in step S1401. In this way, even if the fixation of the target eye of the examinee is unstable, a tomographic image is acquired at substantially the same imaging position as the imaging position acquired in the baseline test. In other words, the information processing system 10 further includes a unit configured to designate a baseline test from previously acquired examinations of the same target eye, and the first three-dimensional motion contrast image of a position that is substantially identical to a tomographic image or a motion contrast image acquired in the baseline test is acquired by referring to a front image acquired in the baseline test.

With the above-described configuration, the information processing apparatus 101 repeats OCTA imaging on different times and dates under substantially the same imaging conditions. Whether to continue the repeat OCTA imaging is determined based on the target value for the repeat OCTA imaging parameter set in the baseline test selected by the operator and the combining condition data of the combined image generated in the baseline test.

In this way, motion contrast data necessary to acquire a desired high-contrast combined motion contrast image is promptly acquired.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-172339, filed Sep. 7, 2017, which is hereby incorporated by reference herein in its entirety.

What is claimed is:

1. An information processing apparatus comprising:
an acquisition unit configured to acquire a three-dimensional optical coherence tomography (OCT) image of a target eye; and
a display control unit configured to display, on a display unit, a first three-dimensional OCT image acquired by the acquisition unit and an interface configured to receive an instruction for acquiring a second three-dimensional OCT image of the target eye, which is an image captured with a same fixation target position as a fixation target position used in capturing the first three-dimensional OCT image and is to be combined with the first three-dimensional OCT image,
wherein the acquisition unit acquires the second three-dimensional OCT image using a setting value identical to a setting value used in acquiring the first three-dimensional OCT image with respect to at least one of a right/left eye selection setting, a main scan direction setting, a scan position setting, a setting of a number of tomographic images to be acquired at a same position, a setting to perform or not perform tracking processing, a setting of a front image for use in tracking, a fixation target position setting and a coherence gate position setting.

2. The information processing apparatus according to claim 1, further comprising a combining unit configured to combine the first three-dimensional OCT image and the second three-dimensional OCT image into a combined image.

3. The information processing apparatus according to claim 2, wherein the combining unit averages the first three-dimensional OCT image and the second three-dimensional OCT image to enhance image quality of the combined image.

4. The information processing apparatus according to claim 1, wherein the first three-dimensional OCT image and the second three-dimensional OCT image are images captured by scanning light in a same main scan direction.

5. The information processing apparatus according to claim 2, wherein the display control unit displays, on the display unit as progress information, at least one of a repeat imaging count, a total number of images acquired by repeat imaging, a number of images judged acceptable among the images acquired by repeat imaging, an imaging condition of the acquired image, evaluation data on the acquired image, and the combined image of the acquired OCT image.

6. The information processing apparatus according to claim 2, further comprising a storage unit, wherein the storage unit saves at least one of the acquired image and the imaging condition of the acquired image or the evaluation data on the acquired image, the acquired OCT image, the combined image, combining condition data on the combined OCT image, and attribute data on the acquired images.

7. The information processing apparatus according to claim 1, wherein, in the acquisition of the second three-dimensional OCT image, the information processing apparatus does not receive an instruction to change the settings, or if an operator instruction to change the setting is received, the information processing apparatus displays a warning on the display unit.

8. The information processing apparatus according to claim 1, further comprising a unit configured to designate a baseline examination from a previously acquired examination of the same target eye,
wherein the first three-dimensional OCT image of a position that is substantially the same as a tomographic image or an OCT image acquired in the baseline test is acquired by referring to a front image acquired in the baseline test.

9. The information processing apparatus according to claim 2, wherein, when the combined image generated by the combining unit is displayed, the display control unit displays, on the display unit as combining condition information, at least one of the repeat imaging count, a number of images used in the combining, a reference image in the combining, a numerical value of an image that indicates a number of times the imaging is performed when the image is acquired, an imaging condition of the image used in the combining, and an evaluation value for the image used in the combining.

10. The information processing apparatus according to claim 1, wherein the three-dimensional OCT image includes a three-dimensional motion contrast image.

11. An information processing method comprising:
acquiring a first three-dimensional OCT image of a target eye; and
displaying on a display unit the first three-dimensional OCT image and an interface configured to receive an instruction for acquiring a second three-dimensional OCT image of the target eye, which is an image captured with a same fixation target position as a fixation target position used in capturing the first three-dimensional OCT image and is to be combined with the first three-dimensional OCT image and is to be combined with the first three-dimensional OCT image, and
receiving the instruction for acquiring the second three-dimensional OCT image of the target eye; and
acquiring the second three-dimensional OCT image using a setting value identical to a setting value used in acquiring the first three-dimensional OCT image with respect to at least one of a right/left eye selection setting, a main scan direction setting, a scan position setting, a setting of a number of tomographic images to be acquired at a same position, a setting to perform or not perform tracking processing, a setting of a front image for use in tracking, a fixation target position setting, and a coherence gate position setting.

12. A non-transitory computer-readable storage medium storing a program for causing a computer to execute the information processing method comprising:
acquiring a first three-dimensional OCT image of a target eye;
displaying on a display unit the first three-dimensional OCT image and an interface configured to receive an instruction for acquiring a second three-dimensional OCT image of the target eye, which is an image captured with a same fixation target position as a fixation target position used in capturing the first three-dimensional OCT image and is to be combined with the first three-dimensional OCT image;
receiving the instruction for acquiring the second three-dimensional OCT image of the target eye; and
acquiring the second three-dimensional OCT image using a setting value identical to a setting value used in acquiring the first three-dimensional OCT image with respect to at least one of a right/left eye selection setting, a main scan direction setting, a scan position setting, a setting of a number of tomographic images to be acquired at a same position, a setting to perform or not perform tracking processing, a setting of a front image for use in tracking, a fixation target position setting, and a coherence gate position setting.

* * * * *